(12) United States Patent
Klein

(10) Patent No.: US 11,852,596 B2
(45) Date of Patent: *Dec. 26, 2023

(54) SYSTEMS FOR PASSIVE MICROWAVE REMOTE SENSING AND THEIR CALIBRATION METHODS

(71) Applicant: Boulder Environmental Sciences and Technology, Boulder, CO (US)

(72) Inventor: Marian Klein, Boulder, CO (US)

(73) Assignee: Boulder Environmental Sciences and Technology, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/085,710

(22) Filed: Dec. 21, 2022

(65) Prior Publication Data

US 2023/0184695 A1    Jun. 15, 2023

Related U.S. Application Data

(63) Continuation of application No. 17/138,268, filed on Dec. 30, 2020, now Pat. No. 11,567,015.

(51) Int. Cl.
| | | |
|---|---|---|
| *G01R 27/04* | (2006.01) | |
| *G01R 27/32* | (2006.01) | |
| *G01N 22/04* | (2006.01) | |
| *G01K 11/00* | (2006.01) | |
| *G01V 3/17* | (2006.01) | |
| *G01N 22/00* | (2006.01) | |
| *G01N 33/28* | (2006.01) | |
| G01R 25/04 | (2006.01) | |
| G01R 27/22 | (2006.01) | |

(52) U.S. Cl.
CPC ........... *G01N 22/04* (2013.01); *G01K 11/006* (2013.01); *G01N 22/00* (2013.01); *G01N 33/2823* (2013.01); *G01V 3/17* (2013.01); G01R 25/04 (2013.01); G01R 27/04 (2013.01); G01R 27/22 (2013.01)

(58) Field of Classification Search
CPC .... G01N 22/04; G01N 22/00; G01N 33/2823; G01K 11/006; G01K 15/005; G01V 3/17; G01W 1/02; G01W 1/18; G01R 27/04; G01R 25/04; G01R 27/22
USPC .......... 324/76.11–76.83, 459, 600, 629, 634, 324/637, 639, 640, 643, 664, 689, 694, 324/696
See application file for complete search history.

(56) References Cited

U.S. PATENT DOCUMENTS

| | | | | |
|---|---|---|---|---|
| 2012/0011947 A1* | 1/2012 | Chen | ...................... | G01N 22/00 73/866.5 |
| 2012/0085909 A1* | 4/2012 | Chen | ...................... | G01N 22/00 250/338.1 |
| 2014/0375335 A1* | 12/2014 | Winso | .................. | G01K 11/006 324/637 |

* cited by examiner

*Primary Examiner* — Raul J Rios Russo

(57) ABSTRACT

A system for passive microwave remote sensing using at least one microwave radiometer includes a fixed body portion, the fixed body portion being configured to attach to a mobile platform, and a mobile body portion, the mobile body portion being configured for rotatably coupling with the fixed body portion for rotation about a rotation axis. The mobile body portion is configured for supporting the at least one microwave radiometer therein such that the at least one microwave radiometer rotates about the rotation axis when the mobile body portion is rotated about the rotation axis such that a polarization axis of the at least one radiometer is aligned with an earth axis. The fixed body portion includes a motor mechanism for effecting rotation of the mobile body portion such that the at least one microwave radiometer provides a vertical scanning below and above the mobile platform.

18 Claims, 15 Drawing Sheets

SYSTEMS FOR PASSIVE MICROWAVE REMOTE SENSING AND THEIR CALIBRATION METHODS

RELATED APPLICATIONS

This application is a Continuation of U.S. patent application Ser. No. 17/138,268, filed 2020 Dec. 30 and titled "SYSTEMS FOR PASSIVE MICROWAVE REMOTE SENSING AND THEIR CALIBRATION METHODS." The above referenced application is incorporated herein by reference in its entirety.

STATEMENT REGARDING FEDERALLY SPONSORED RESEARCH OR DEVELOPMENT

This invention was made with government support under contract numbers DG133R06CN0156 awarded by National Oceanic and Atmospheric Administration, grant number 944622 awarded by National Science Foundation, and grant numbers DE-FG02-08ER85166, DE-SC0010160, DE-SC0015068, DE-SC0015964, and DE-SC0019639 awarded by the U.S. Department of Energy. The government has certain rights in the invention.

FIELD OF THE INVENTION

This invention relates generally to systems for remote sensing and, more specifically, to systems implementing passive microwave remote sensing, also known as radiometers or radiometry, their observation modes, and calibration methods.

DESCRIPTION OF THE BACKGROUND

Remote sensing instruments, and more particularly, passive microwave remote sensing instruments, also known as microwave radiometers, can be used to remotely observe an environment. Passive microwave radiometers remotely observe an environment by measuring the radiant flux of electromagnetic radiation received from the environment. Depending on the environment being observed, these measurements are used to determine various properties of the environment, such as surface and/or atmospheric parameters (e.g., temperature, humidity, cloud water content, soil moisture, and snow cover).

Various types of remote sensing instruments are currently available. Surface-based remote sensing instruments operate at or near the Earth's surface, and are installed on the ground, a land structure (e.g., a building), a land craft (e.g., an automobile), a nautical structure (e.g., a buoy), or a watercraft (e.g., a boat). Atmospheric-based remote sensing instruments operate within the Earth's atmosphere and over the Earth's surface, and are installed on an aircraft, such as an airplane, a helicopter, a balloon, a dirigible, unmanned aircraft, unmanned autonomous vehicle, and the like. Space-based remote sensing instruments operate from space, and are installed on spacecraft (e.g., a satellite).

A microwave radiometer, or a passive microwave remote sensor, for the purpose of this disclosure, generally has three main parts: an antenna, a receiver, and a data acquisition and processing system. An antenna focuses the radiant flux of electromagnetic radiation into the receiver. A receiver converts the incoming radiant flux into a signal, usually proportional to the input power. The signal is read, processed, and stored by the data acquisition system into desired measurements. A microwave radiometer may receive the signal in a single polarization or in multiple polarizations. The terms "radiometer" and "microwave radiometer" are used interchangeably in the present disclosure.

Passive microwave radiometers have been in use since at least the 1960s. For example, the Mariner 2 spacecraft used a passive microwave radiometer to map the atmospheric temperature of Venus in 1962. Further, passive microwave radiometers have been implemented for Earth-centric observations at least as early as 1968. Today, space-based passive microwave radiometers are regularly used for weather forecasting and for other environmental observations of Earth. However, use of surface-based and atmospheric-based passive microwave radiometers has been largely limited to experimental and scientific environmental observation.

SUMMARY OF THE INVENTION

In accordance with embodiments described herein, a system for passive microwave remote sensing using at least one microwave radiometer is described. The system includes a fixed body portion and a mobile (i.e., scanning) body portion. The mobile body portion is configured for rotatably coupling with the fixed body portion for rotation about one or two rotation axes. The mobile body portion is further configured for supporting the microwave radiometer therein such that the microwave radiometer rotates about the rotation axis when the mobile body portion is rotated about the rotation axis. The fixed body portion includes a motor mechanism for effecting rotation of the mobile body portion.

In another embodiment, a method for remote sensing using a remote sensing system is disclosed. The method includes providing a fixed body portion and a mobile body portion as a part of the remote sensing system. The mobile body portion is rotatably coupled with the fixed body portion for rotation about a mobile body axis over a range of rotation angles. The mobile body portion is further configured for supporting and at least partially enclosing at least one radiometer therein. The method further includes rotating the mobile body portion about the mobile body axis such that the radiometer is thereby rotated about the mobile body axis while sensing incoming radiant flux of electromagnetic radiation incident thereon over the range of rotation angles.

In an embodiment, the at least one radiometer includes an antenna, a sensor, and a data acquisition system, and the method further includes using the antenna to focus incoming radiant flux of electromagnetic radiation to the receiver, using the sensor to convert the incoming radiant flux of electromagnetic radiation to a signal readable by an external device, such as a computer, and using the data acquisition system to read the signal.

In a further embodiment, the method includes providing an internal calibration standard or standards for the radiometer, and determining whether an external calibration opportunity has been detected. If a calibration opportunity has been detected, the method includes scanning a first external calibration target with the at least one radiometer and scanning a second external calibration target with the radiometer to generate first and second external calibration target scans. The method further includes measuring a temperature of the internal calibration standard, and determining an adjustment to the internal calibration standard based on the first and second external calibration target scans so as to determine a most accurate calibration basis. The method includes using the most accurate calibration basis for calibrating the radiometer.

BRIEF DESCRIPTION OF THE DRAWINGS

To facilitate further description of the embodiments, the following drawings are provided in which.

Figure 1:
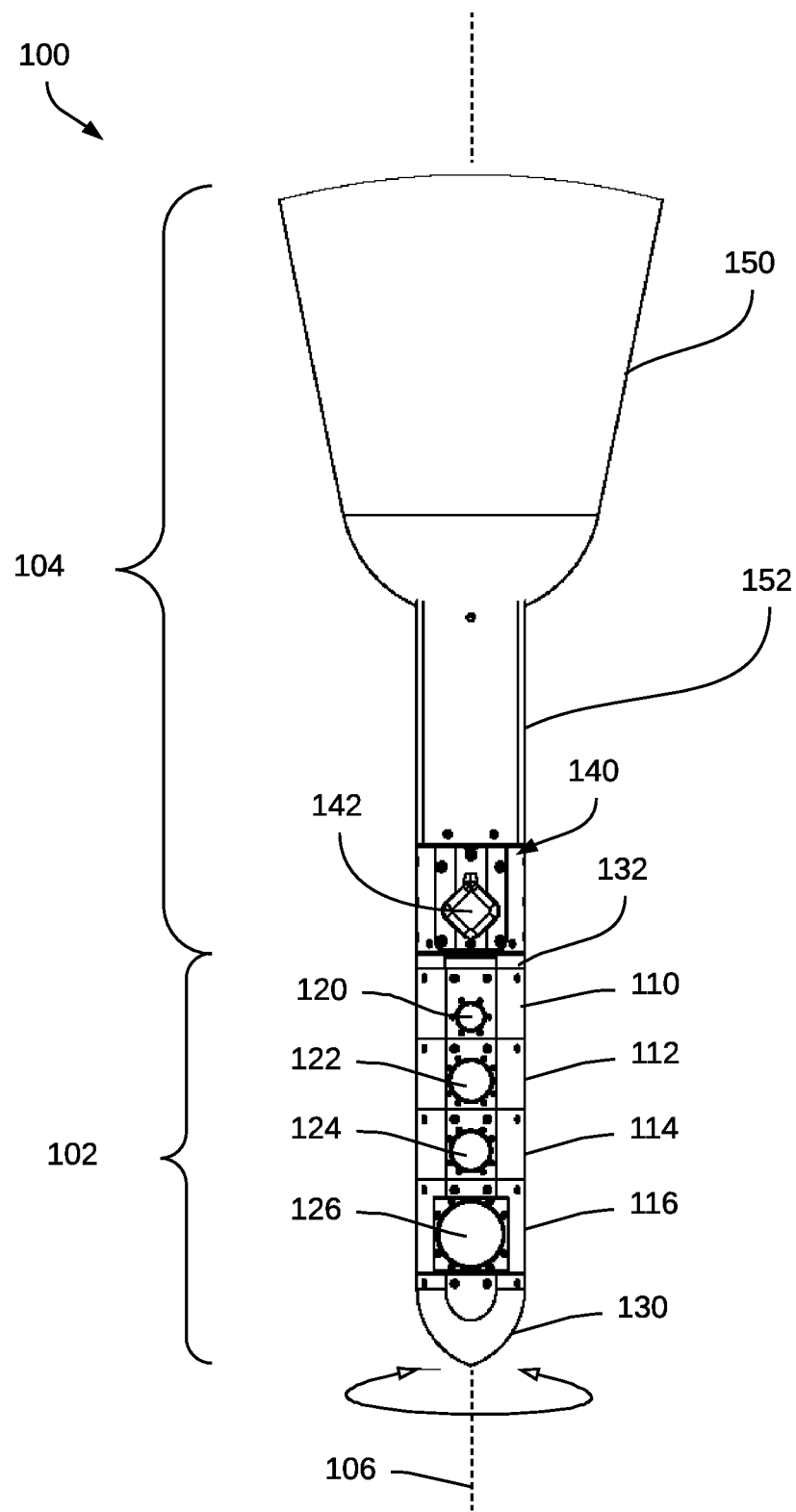
FIG. 1 illustrates a top view of a system for remote sensing, such as for installation on an aircraft, according to an embodiment.

For simplicity and clarity of illustration, the drawing figures illustrate the general manner of construction, and descriptions and details of well-known features and techniques, some details may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

DETAILED DESCRIPTION OF EMBODIMENTS OF THE INVENTION

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable. Turning to the drawings, FIG. 1 illustrates a top view of system 100 for remote sensing, according to an embodiment. For example, system 100 can be implemented for passive remote sensing of an environment. In the exemplary embodiment illustrated in FIG. 1, system 100 includes a mobile body portion 102 and a fixed body portion 104. Mobile body portion 102 is configured for rotation up to 360-degrees about a rotation axis (indicated by a dashed line 106). Mobile body portion 102 includes one or more body sections (indicated as body sections 110, 112, 114, and 116 in the exemplary system 100).

Each one of body sections 110, 112, 114, and 116 includes, for example, one of radiometers 120, 122, 124, and 126. For instance, each one of radiometers 120, 122, 124, and 126 is configured for detecting electromagnetic signals in a different wavelength range varying from each other one of the radiometers. Alternatively, some or all radiometers can operate within the same wavelength range and multiple beams could be used to improve spatial resolution, sampling. One or more of radiometers 120, 122, 124, and 126 can be a passive microwave radiometer. Each one of radiometers 120, 122, 124, and 126 includes an antenna (illustrated as a lens antenna), which can for example be aligned perpendicularly to rotation axis 106, and parallel to or co-planar to each other antenna. Each one of body sections 110, 112, 114, and 116, for example, is enclosed with a lens to protect internal electronics such as the radiometer contained therein, while permitting electromagnetic radiation of interest to pass therethrough to measure the radiant flux of the electromagnetic radiation. While mobile body portion 102 is shown with four body sections, each including a radiometer, other embodiments may include more or fewer numbers of body sections, and the body sections may include devices other than radiometers, such as other types of environmental sensors. Additionally, body sections 110, 112, 114, and 116 can be modular such that each body section is interchangeable with each other body section as well as removable for replacement or repairs. In an example, any number of body sections can be connected in series in any order as modular blocks. Furthermore, each body section can be configured to rotate independently of each other, or all body sections can be configured to rotate together. In other words, multiple radiometers for observation of multiple bands of the electromagnetic spectrum can readily integrated into the body sections of system 100, thus providing interchangeability and customizability for allowing the use of system 100 in a variety of settings.

Additionally, each body section can include lenses and/or covers to protect any internal instruments installed therein. The lenses and/or covers can be formed of suitable materials that provide protection of internal instrumentation while transmitting therethrough the electromagnetic radiation of interest. Suitable materials include, but are not limited to, polystyrene (e.g., Rexolite®), polytetrafluoroethylene (e.g., Teflon®), polymethylpentene (e.g., TPX®), and the like. The lenses and covers are operable as an interface between the internal instrument volume of the radiometer and the external, ambient environment. In certain embodiments, the plastic material implemented for the lens/cover can be operable in an environment without significant deterioration of the dielectric properties of the plastic material. In certain embodiments, the internal instrument volume of each body section can be sealed and/or pressurized to protect the internal instrumentation from external environment influences, such as, for example, from water.

Mobile body portion 102 optionally includes a nose cone 130, which is configured for improving the aerodynamics of system 100 when mounted, for instance, at the nose of an airplane. Further, mobile body portion 102 optionally includes a drive plate 132 configured for facilitating the rotational motion of mobile body portion 102.

Fixed body portion 104 includes an end section 140, onto which mobile body portion 102 is attached. End section 104 is configured to rotatably engage mobile body portion 102 such that mobile body portion 102 is able to freely rotate about rotation axis 106. End section 140 can also include electronic elements, such as a global positioning system (GPS) 142 for tracking the location and timing of system 100. Other instruments, such as systems for tracking ambient (e.g., atmospheric, such as pressure, temperature, humidity and other) variables or inertial measurements for instance, can also be included in fixed body portion 104 or even in mobile body portion 102.

Fixed body portion 104 can also include a receiving element 150 for attachment to a moving system (not shown) for transporting system 100 within which environmental characteristics will be collected by system 100. For example, receiving element 150 can be configured for attachment to a nose section of a spacecraft, an aircraft, a land craft, a watercraft, a nautical buoy, a balloon, or a building. Receiving element 150 can be appropriately shaped for attachment to other moving systems, such as unmanned aerial vehicles. Optionally, fixed body portion 104 includes a standoff section 152 to separate mobile body portion 102 from receiving element 150. Standoff section 152, for instance, provides additional physical separation of the radiometers contained in mobile body portion 102 for further separation from the moving system, onto which system 100 is attached.

To rotate mobile body portion 102 with respect to fixed body portion 104, system 100 further includes one or more motors or other suitable mechanism (not shown) for providing the rotational force. Additional components, such as gears and sprockets, also not shown, can be implemented for engaging mobile body portion 102 with a motor. The motor can be located, for instance, within fixed body portion 104, and can be configured to rotate mobile body portion 102 as a whole or independently rotate one or more of body sections 110, 112, 114, and 116. The rotational speed provided by the motor can be adjusted based on the desired scan rate, observation type, size and weight of mobile body portion 102, and/or the work capacity of the motor.

While the various components in mobile body portion 102 is shown to rotate about rotation axis 106, which is shown coaxial to fixed body portion 104, other orientations of the rotation axis are possible, as will be discussed in further detail below with respect to additional embodiments. For example, if system 100 is attached to a nose of an aircraft, for example, rotation axis 106 would be parallel to a ground surface of the earth (and a flight line). Alternatively, system 100 can be configured such that rotation axis 106 of mobile body portion 102 is oriented at oblique angles with respect to the earth such that the radiometers are able to measure the radiant flux of the electromagnetic radiation at different orientations. It is noted that the rotation of mobile body portion 102 can also serve to prevent water (e.g., from cloud particles) from remaining on the surface of the lens covers while protecting the internal instrumentation within mobile body portion 102 from condensation and particulate contamination. These characteristics allow cost savings due to the elimination of hydrophobic coatings, air blowers, and other water or humidity condensation management mechanisms.

Figure 2:
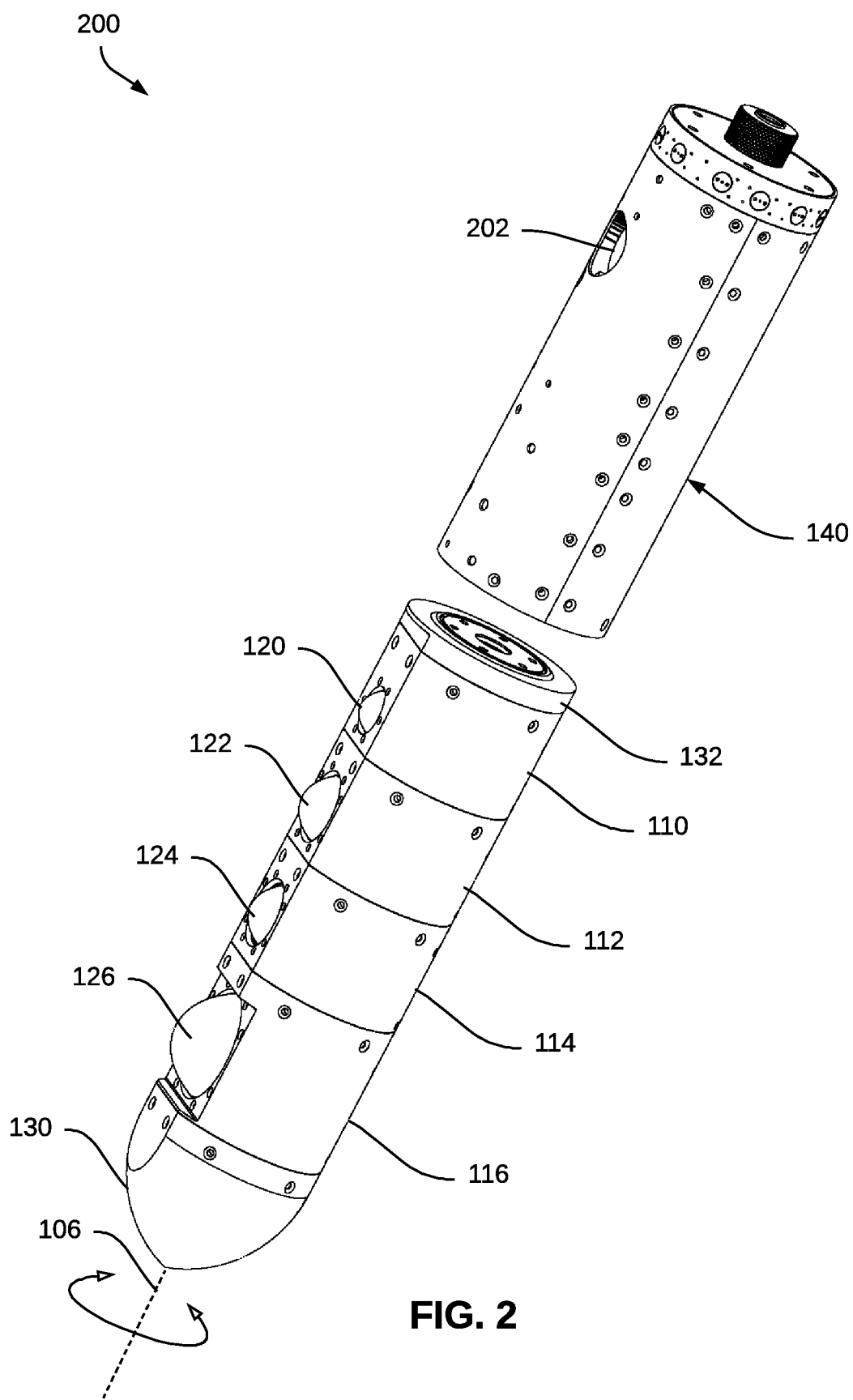
FIG. 2 illustrates an exploded, perspective view of a portion of the system of FIG. 1.

Further details of mobile body portion 102 and end section 140 of fixed portion 104 are illustrated in FIG. 2. As shown in FIG. 2, each one of radiometers 120, 122, 124, and 126 have different characteristics from each other so as to be capable of measuring a variety of environmental factors. Also, end section 140 includes a cavity 202 for attachment of standoff section 152 (not shown). GPS 142 is not shown in FIG. 2 for illustrative clarity.

It is emphasized that the ability of system 100 to provide a full 360-degrees vertical scan is an important aspect of the described embodiments. By rotatably attaching mobile body portion 102 to fixed body portion 104, the radiometers installed in mobile body portion 102 is able to provide continuous vertical (also known as cross-track, sounding, or elevation) scanning of substantially the whole atmosphere, below and above the mobile platform to which system 100 is attached. The ability to provide the full 360-degrees vertical scan allows continuous environmental sensing over a wide field of view, for example, providing information from each radiometer on the atmosphere and surface parameters during one scan. The modularity of being able to add or remove body sections allows degrees of customization not possible with currently available environmental sensing devices. Furthermore, the continuous vertical scanning ability also provides additional advantages in the calibration of the various environmental sensing instruments disposed within mobile body portion 102, as will be described in more detail below. The vertical scan may also be less than 360-degrees, while 180-degrees or greater and ability to observe below and above aircraft may provide additional advantages to system 100.

Figure 3:
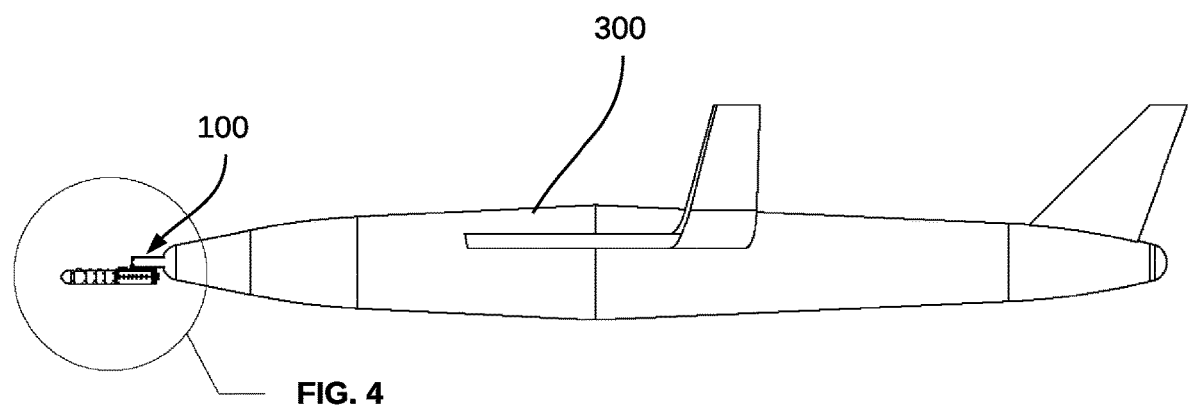
FIG. 3 illustrates a side view of the system of FIG. 1 as attached to an aircraft.
Figure 4:
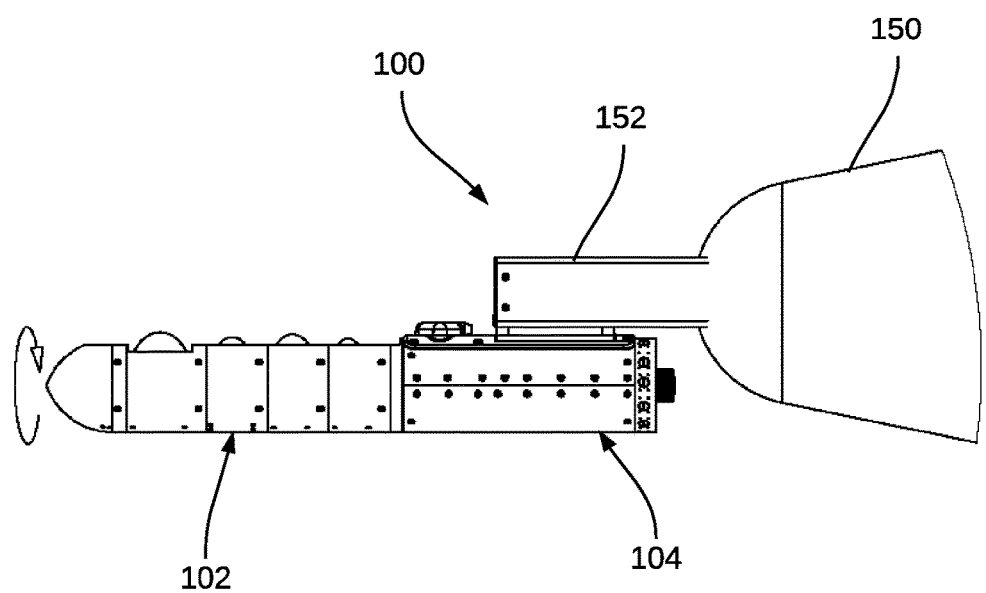
FIG. 4 illustrates an enlarged view of a portion of the system of FIG. 3.

FIGS. 3 and 4 show a side view of system 100 as attached to an aircraft 300. As particularly visible in FIG. 4, the relative orientation of mobile body portion 102, fixed body portion 104, receiving element 150, standoff section 152 is such that receiving element 150 is securely affixed to aircraft 300, while mobile body portion 102 is able to freely rotate with respect to fixed body portion 104. Alternatively, receiving element 150 can be configured for attachment to another portion of the aircraft, such as a wing or tail using, for example, an aircraft pylon.

In operation, system 100 offers numerous advantages over conventional systems for remote sensing, which often have limited observational capabilities, are undesirably bulky, consuming excessive power, operate slowly, be difficult to calibrate and/or maintain, be limited to observing a single band of the electromagnetic spectrum, over a small range of angles, below or above the platform, be costly to operate, and/or mix the polarization axes of the observed electromagnetic radiation during the observation process due to the use of reflective mirror motions, instead of the whole antenna rotation. As system 100 is modular, compact, allow observation of multiple bands of the electromagnetic spectrum, cost-effective, and provide accurate measurements of electromagnetic radiation without mixing the polarization axes of the observed electromagnetic radiation, system 100 can be effectively implemented in a variety of settings, including spaced-based, surface-based, and atmospheric-based observations of an environment.

Additionally, the antennas of the radiometers installed in mobile body portion 102 can be aligned perpendicularly with respect to the surface of the earth as the radiometers are rotated about rotation axis 106. Thus, the polarization of the electromagnetic radiation received by the antennas can remain undisturbed with respect to the earth's axes during observation. For instance, certain surface features or cloud particles within the observed environment can alter the polarization state of electromagnetic radiation incident thereon. Whereas a conventional radiometer may require, for example, a mirror arrangement to reflect and focus observed electromagnetic radiation onto its antennas, the radiometer antennas of system 100 can be pointed directly at the electromagnetic radiation of interest. Such mirror arrangements often exhibit undesirable aerodynamic characteristics, are cumbersome to reposition, and constrained in rotatability. Consequently, system 100 allows observation of the electromagnetic radiation with the same polarization as emitted from the environment being observed with greater scan efficiency than conventional remote sensing systems with reflecting mirrors. Further, the rotatability of mobile body portion 102 and elimination of reflecting mirror arrangements allows for direct aiming at objects of interest and quick scanning of the observed environments much more readily than conventional remote sensing systems. Still further, the dual polarization of each receivers can be also used as an indicator of the proper operation of the radiometer. For any state of the atmosphere, the polarization signal should be substantially the same for horizontal and vertical polarizations at zenith, thus, any variations between two receivers (i.e., one for each polarization) can be an indication of a problem with one of the radiometers.

Figure 5:
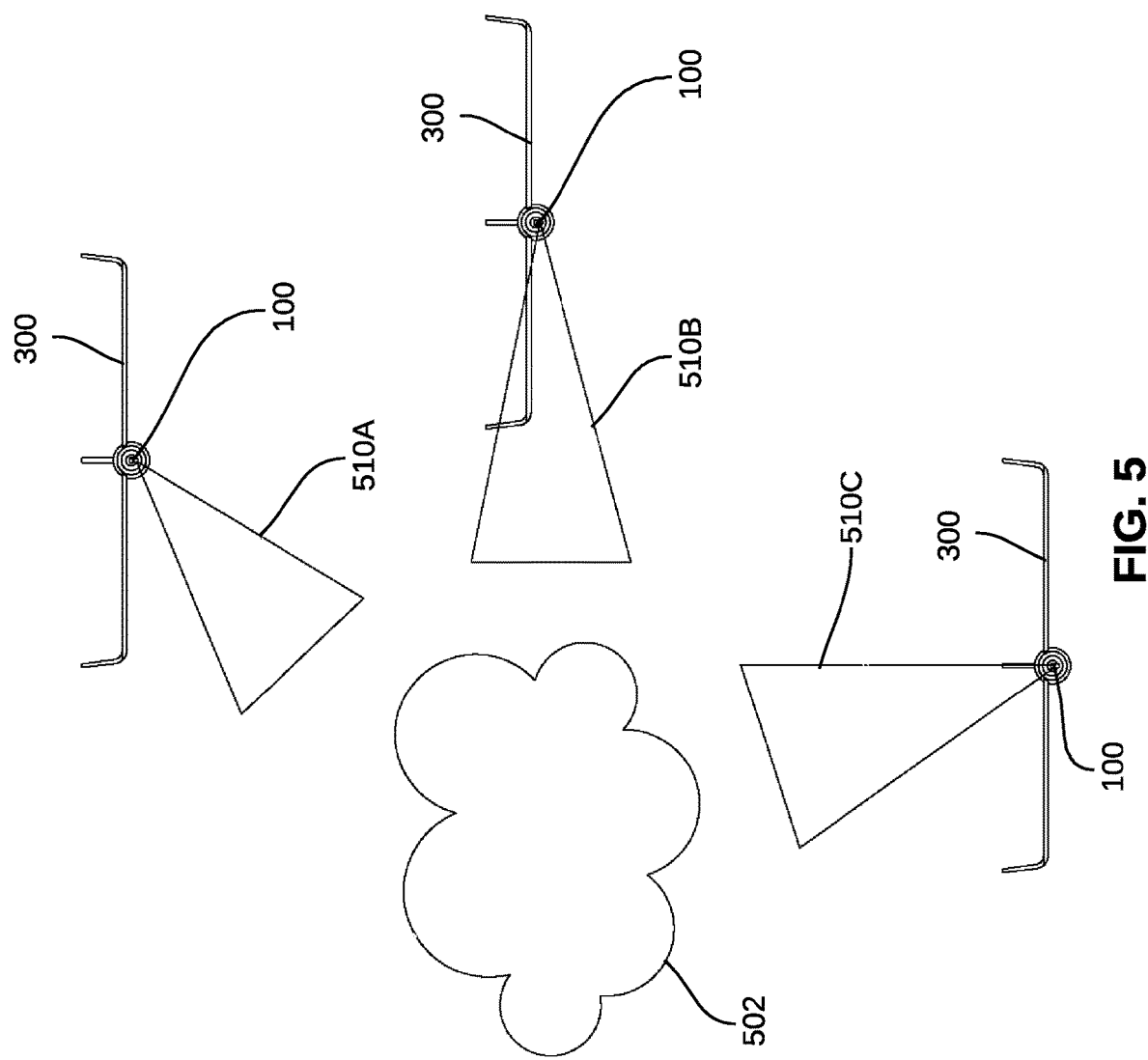
FIG. 5 illustrates the system of FIG. 1 observing a cloud by receiving electromagnetic radiation at multiple orientations.

Referring now to FIG. 5, FIG. 5 illustrates the system of FIG. 1 observing a cloud by receiving electromagnetic radiation at multiple orientations. As shown in FIG. 5, the remote sensing system shown in FIGS. 1-4 can be used to monitor a cloud 502 from different altitudes and observation angles. As shown in FIG. 5, system 100 mounted on aircraft 300 at an altitude above cloud 502 can be configured to observe cloud 502 over a first antenna beam 510A. That is, mobile body portion 102 of system 100 is aimed to observe cloud 502 over first antenna beam 510A. Subsequently or alternatively, when aircraft 300 is located side-by-side with cloud 502, mobile body portion 102 of system 100 can be aimed to observe cloud 502 over a second antenna beam 510B. Again, subsequently or alternatively, when aircraft 300 is located at an altitude below cloud 502, mobile body portion 102 of system 100 can be rotated to observe cloud 502 from below over a third antenna beam 510C. Thus, system 100 is capable of scanning a full planar volume of an environment, unlike conventional remote sensing systems in which the radiometer orientations are fixed or can observe much narrower section of degrees than the 360-degrees aircraft view.

Figure 6:
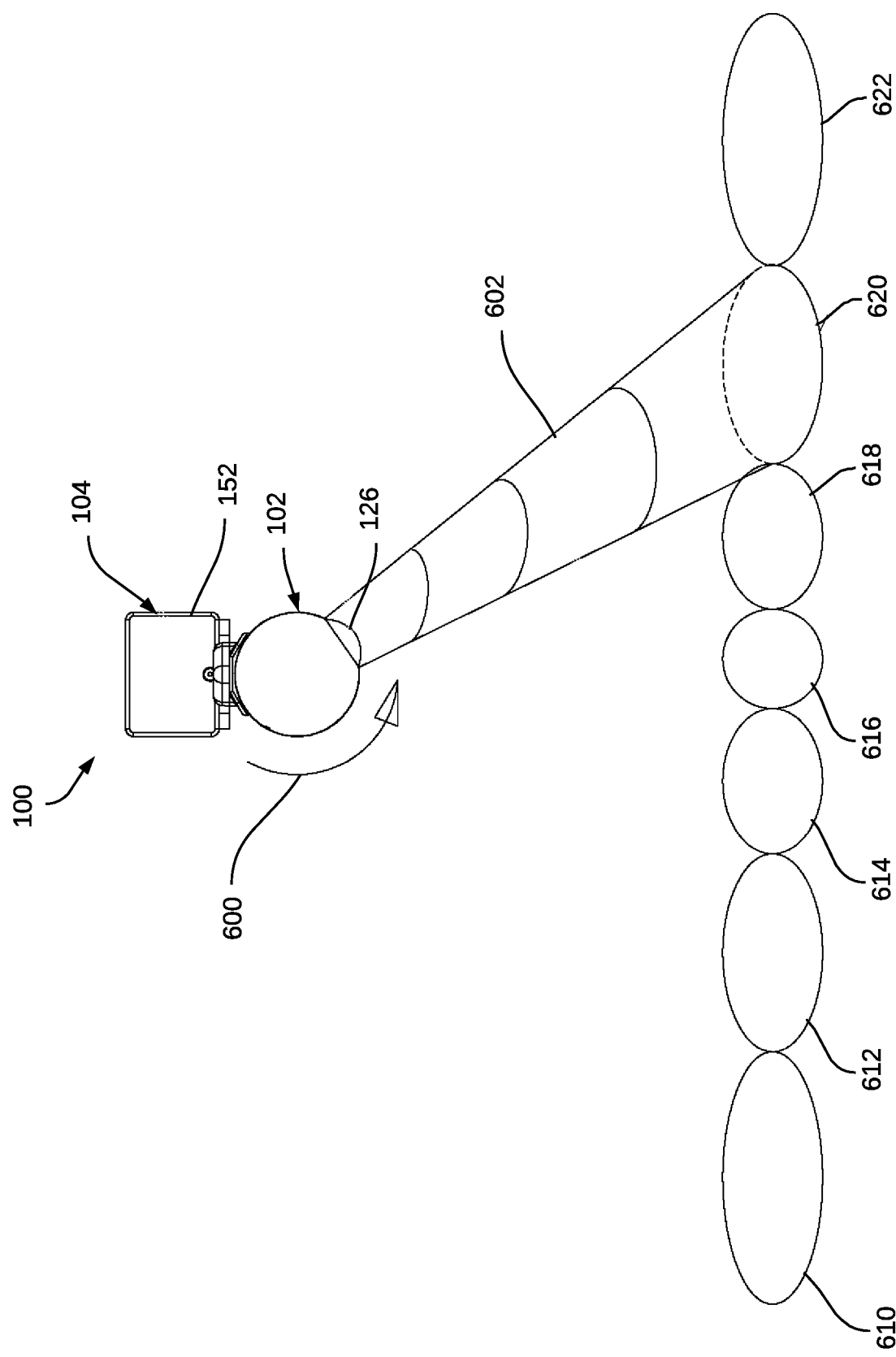
FIG. 6 illustrates footprints of antenna beams of a system for remote sensing, according to an embodiment.

Turning to FIG. 6, the moving footprints of the antenna beams of system 100 as mobile body portion 102 is rotated during environmental observation. As mobile body portion 102 is rotated in a direction indicated by an arrow 600, antenna beam 602 scans over a range indicated by adjacent footprints 610, 612, 614, 616, 618, 620, and 622. While footprints 610, 612, 614, 616, 618, 620, and 622 are shown as distinct circular areas, the radiometers in mobile body portion 102 can be configured for scanning and sampling over a continuous area, for example, from footprint 610 through footprint 622. The diameters of the footprints vary in size, depending on the mobile body portion 102 (and thus the radiometers contained therein) angle and the distance of the radiometers from the surface to be observed.

Figure 7:
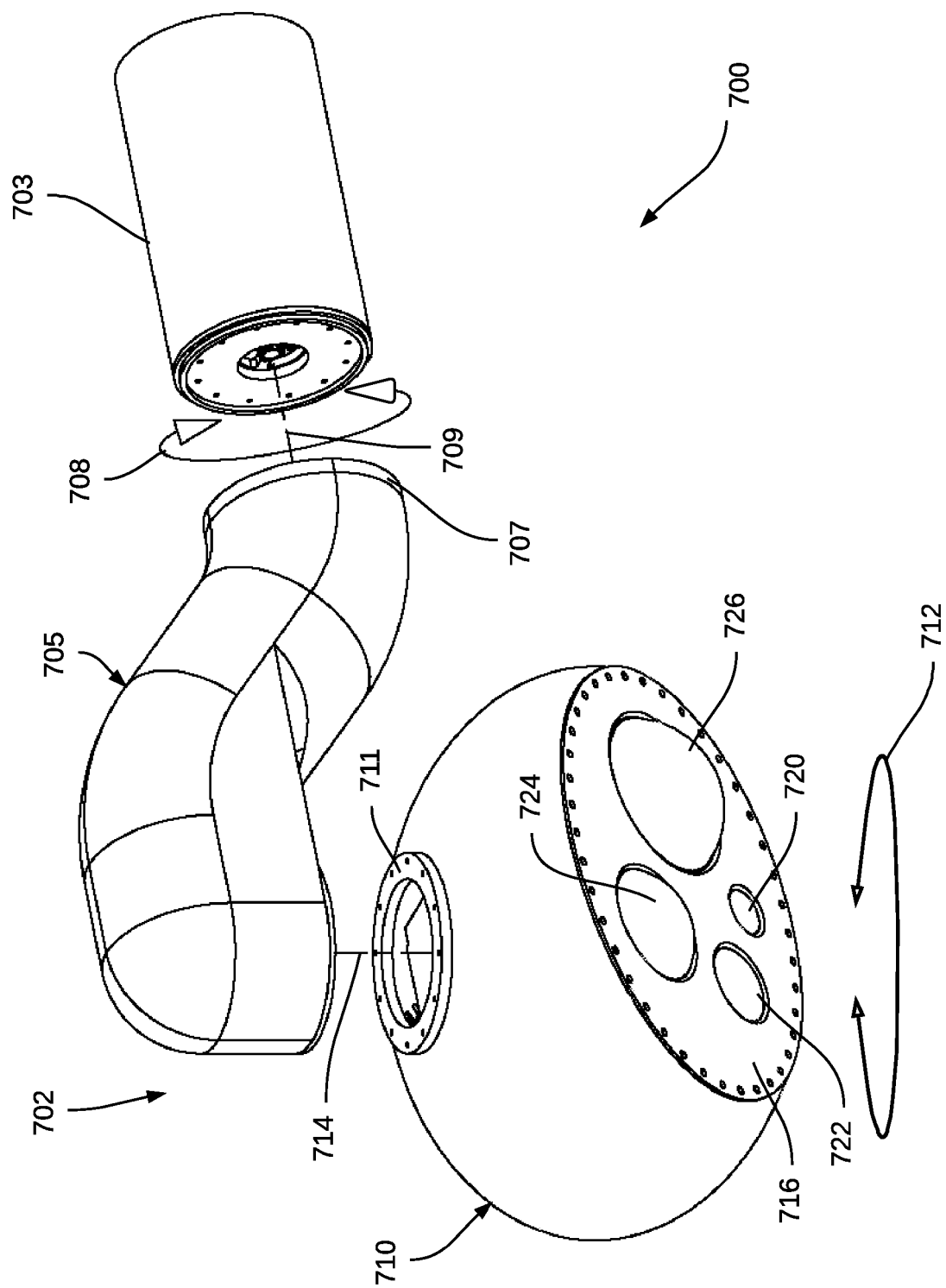
FIG. 7 illustrates an exploded, perspective view of a dual axes scanning system for remote sensing, according to an embodiment.

FIG. 7 illustrates an exploded, perspective view of a dual axes scanning system 700 for remote sensing, according to an embodiment. Like system 100, system 700 includes a mobile body portion 702 and a standoff section 703. Standoff section 703 can be, for example, part of a larger fixed body section, as in system 100. However, mobile body portion 702 is split into two parts that are rotatable about two separate rotation axes. A first mobile section 705 is rotatably coupled to standoff section 703 via a first coupler 707. First mobile section 705 is configured for rotation (indicated by a double-headed arrow 708) along a first rotation axis 709 coaxial to standoff section 703. A second mobile section 710 is rotatably coupled to first mobile section 705 via a second coupler 711 such that second mobile section 710 is rotatable (indicated by a double-headed arrow 712) about a second rotation axis 714. As shown in FIG. 7, second rotation axis 714 is perpendicular to first rotation axis 709. Alternatively, second mobile section 710 can be mounted such that second rotation axis 714 is at an oblique angle with respect to first rotation axis 709.

Second mobile section 710 includes at least one face 716, into which one or more radiometers are installed. In the example illustrated in FIG. 7, face 716 includes four radiometers 720, 722, 724, and 726. The radiometers can be designed to observe in various wavelengths and provide simultaneous observations over wide microwave spectrum. Alternatively, some or all radiometers can operate within the same wavelength range and multiple beams could be used to improve spatial resolution, sampling. Optionally, second mobile section 710 includes one or more additional faces, into which additional radiometers are installed. If multiple faces are included in second mobile section 710, the faces can be similar to each other or have distinct shapes configured for specific radiometer or other instruments to be included therein. In an example, multiple faces are disposed circumferentially equidistant about second mobile section 710. System 700 is rotatable about both first rotation axis 709 and second rotation axis 714. Thus, system 700 has gained an additional degree of freedom in the directionality of radiometers 720, 722, 724, and 726. Further, similarly to system 100, the rotation of first and second mobile sections 705 and 710 enable removal of condensation and/or particulate contamination during a flight.

Figure 8:
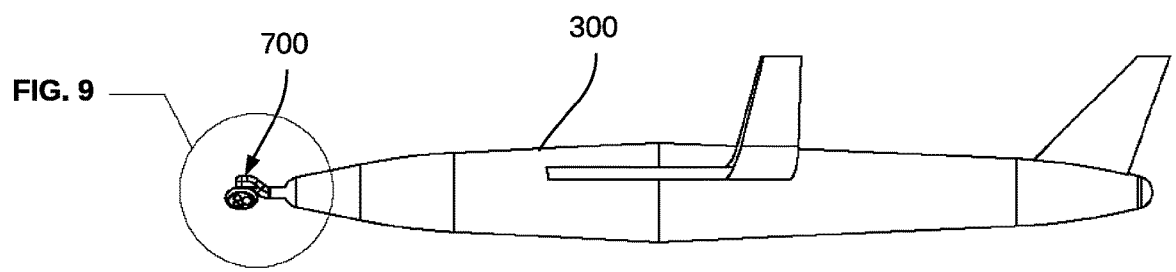
FIG. 8 shows a side view of the system of FIG. 7 as attached to an aircraft.
Figure 9:
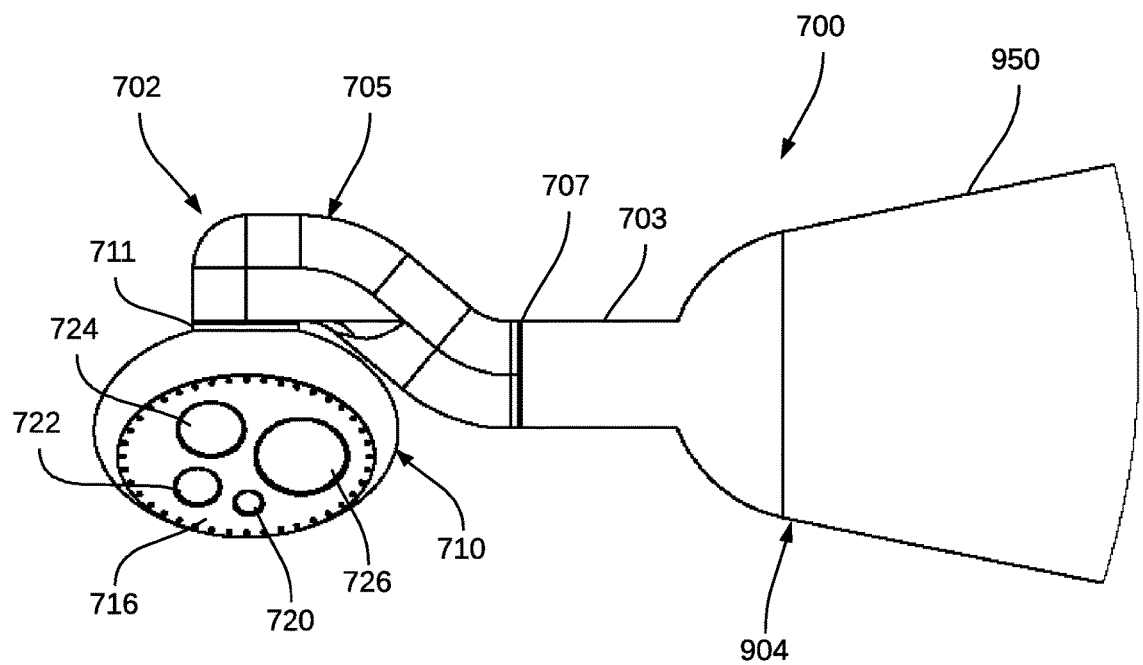
FIG. 9 illustrates an enlarged view of a portion of the system of FIG. 8.

FIGS. 8 and 9 illustrate system 700 as attached an aircraft. As shown in FIG. 8, system 700 is attached to aircraft 300, as was shown in FIG. 3. As shown in greater detail in FIG. 9, standoff section 703 is part of a larger fixed body portion 904, which also includes a receiving element 950. Receiving element 950 is configured for secure attachment onto aircraft 300 while first mobile section 705 and second mobile section 710 of mobile body portion 702 are freely rotatable with respect to fixed body portion 904. Mobile body portion 702 and fixed body portion 904 contain mechanisms, such as motors, for rotating first and second mobile sections 705 and 710, respectively.

Figure 10:
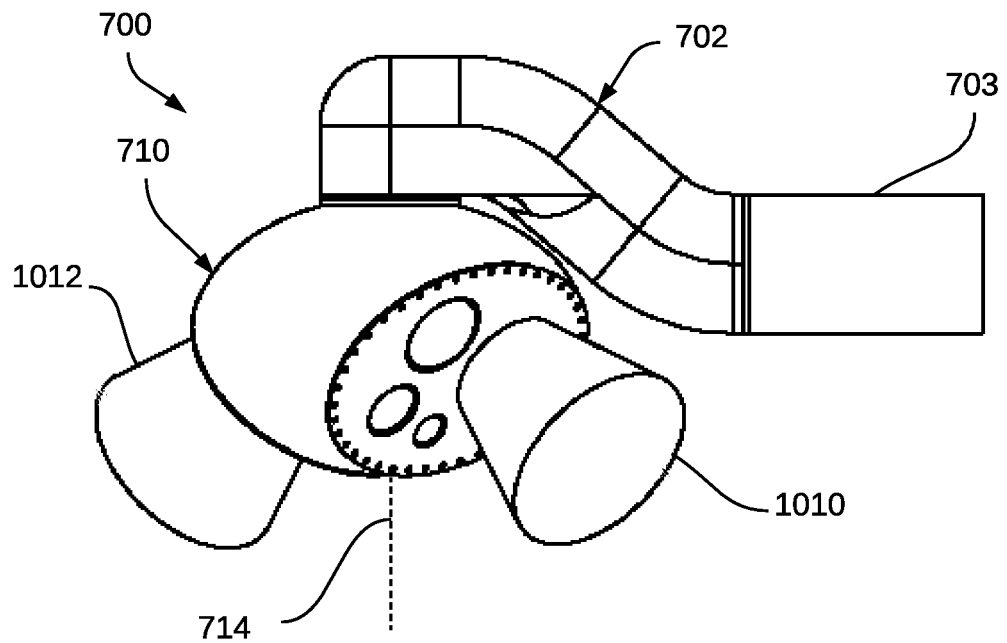
FIGS. 10 and 11 illustrate the system of FIG. 7 observing an environment in an azimuthal mode and receiving electromagnetic radiation from multiple beams at multiple orientations.
Figure 11:
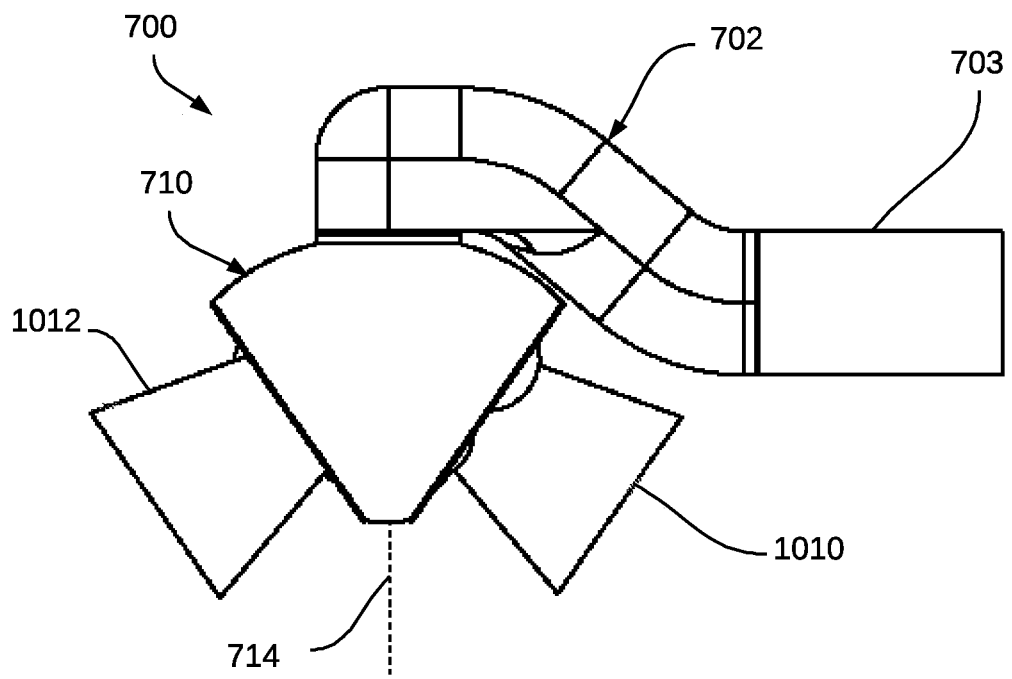

FIGS. 10 and 11 illustrate different orientations of second mobile section 710 as second mobile section 710 is rotated about second rotational axis 714. As shown in FIGS. 10 and 11, a first antenna beam 1010 and second antenna beam 1012 correspond to radiometers integrated into two opposing faces of second mobile section 710. First and second antenna beams 1010 and 1012, respectively, point toward different areas of the environment being observed as second mobile section 710 is rotated about second rotation axis 714.

Figure 12:
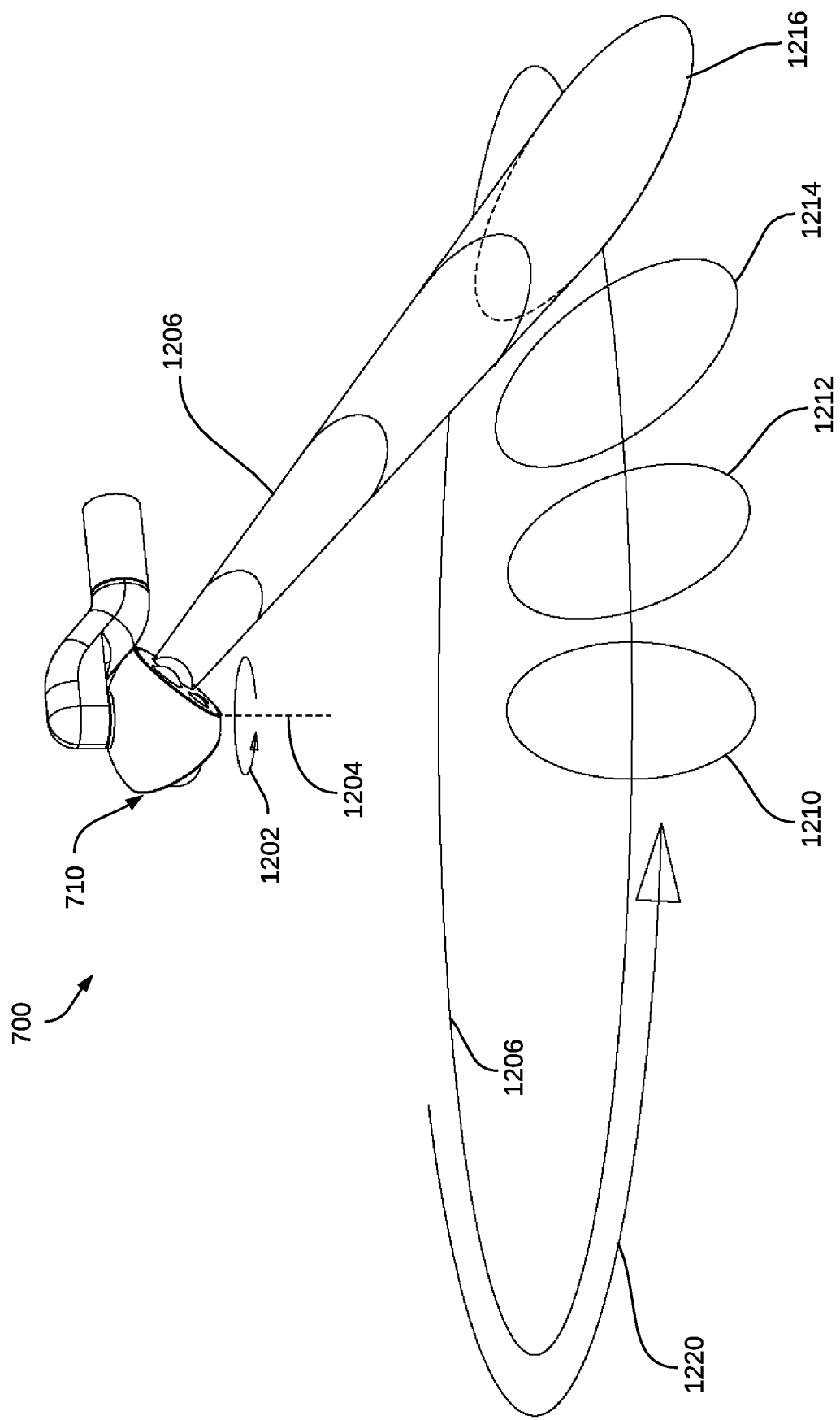
FIG. 12 illustrates the system of FIG. 7 observing an environment in an azimuthal mode by receiving an electromagnetic radiation from radiometer antenna beams of the system.

FIG. 12 illustrates the observational footprints of system 700 as second mobile section 710 is rotated in a direction 1202 about an azimuthal axis 1204, perpendicular to a surface being observed (represented by an oval 1206). As second mobile section 710 is rotated in direction 1202, one of the radiometers integrated into second mobile section 710 performs measurements via antenna beam 1206 over adjacent footprints 1210, 1212, 1214, and 1216 in a direction 1220. Unlike system 100, the radiometers of system 700 are able to maintain a constant incidence angle (i.e., an angle defined between the radiometer beams and surface 1206 while the radiometers are rotated azimuthally). A constant incident angle is usually used for surface observations, or imaging, thus FIG. 12 illustrate the system 700 operation in an imaging (i.e., conical or azimuthal scan) mode.

Figure 13:
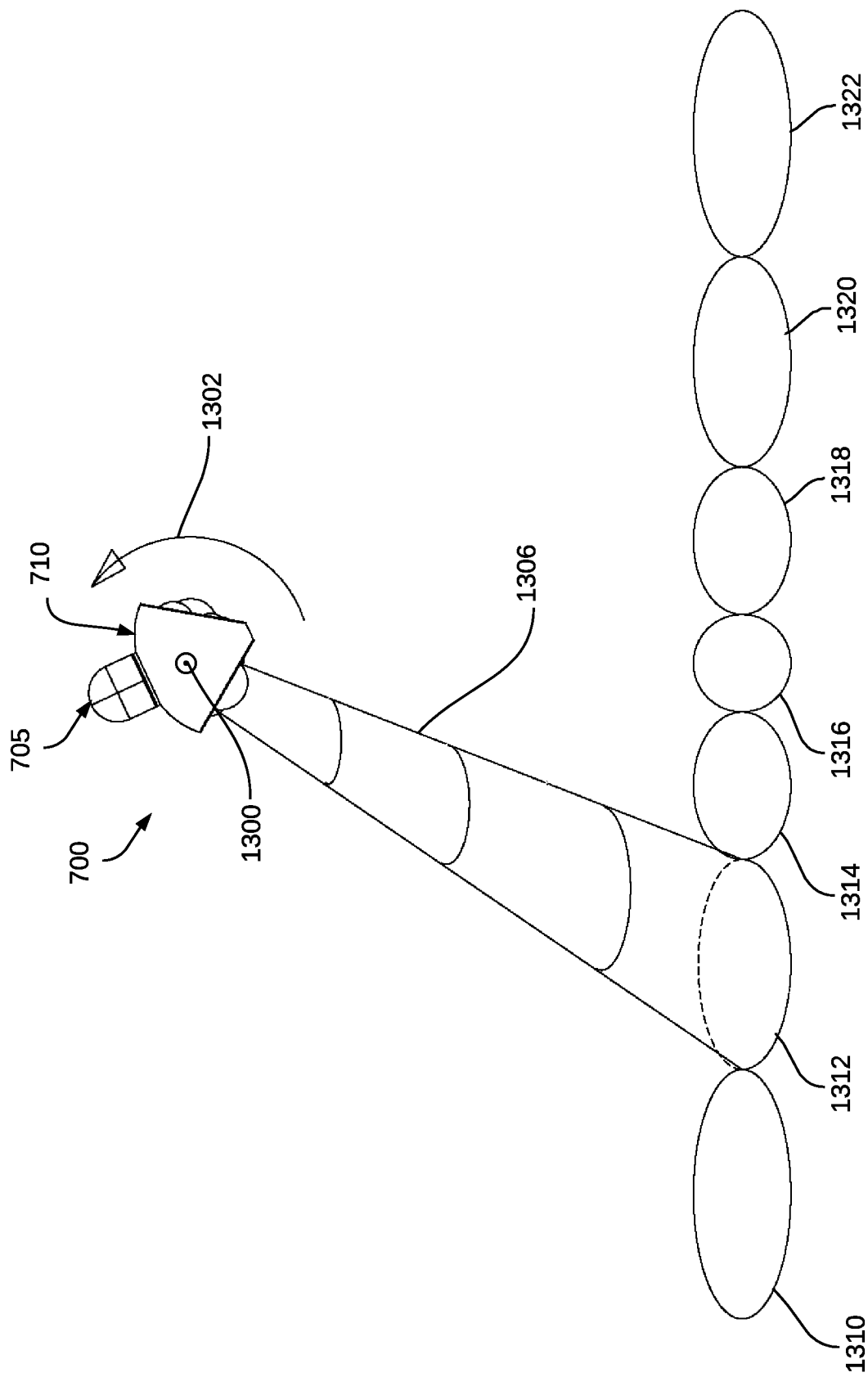
FIG. 13 illustrates the system of FIG. 7 observing an environment in an elevation mode by receiving an electromagnetic radiation from radiometer antenna beams of the system.

In contrast, FIG. 13 illustrates the system of FIG. 7 observing an environment in an elevation mode by receiving an electromagnetic radiation from radiometer antenna beams of the system from a plane perpendicular to the earth surface (and the flight line). Such operational mode is usually used for observations of atmosphere, often referred to as sounding or cross-track scan mode. In FIG. 13, first mobile section 705 is rotated along a rotation axis (represented by a dot 1300) parallel to the surface being observed in a direction 1302. In this way, one of the radiometers integrated into second mobile section 710 performs measurements via antenna beam 1306 over adjacent footprints 1310, 1312, 1314, 1316, 1318, 1320, and 1322, in a manner similar to the motion of system 100 illustrated in FIG. 6. Additionally, azimuthal rotation illustrated in FIG. 12 can be combined with rotation in elevation mode to provide further flexibility in remote sensing of the environment. Thus, the observation from a single system, such as 700, and using one set of radiometers (i.e., sensors) can provide information on the composition of the atmosphere above the aircraft, below the aircraft and also characterize the surface emissions accurately at almost the same time, with similar spatial resolution. In other words, the whole radiation environment can be characterized at once.

System 700 illustrated above can be configured with removable faces, for example, to permit customized arrangement and replacement of radiometers and other sensors placed therein. First and second mobile sections 705 and 710 can be configured for rotation at any suitable speed sequentially or simultaneously. The rotation speeds are customizable to the specific observation conditions desired (e.g., aircraft altitude, flight speed), such as the scan rate of the one or more radiometers, type of observations desired, size of first and second mobile sections 705 and 710, the available energy supply for system 700, the work capacity of the motor(s) and machinery used to effect the rotations, and other factors. System 700 provides some or all of the same advantages that system 100 provides over conventional remote sensing systems. For instance, system 700 is capable of observing multiple bands of the electromagnetic spectrum without disturbing the polarization states of the observed electromagnetic radiation, enabling multiple polarization observations. Additionally, system 700 can be more compact, less expensive, and more operationally efficient than conventional systems for remote sensing.

Figure 14:
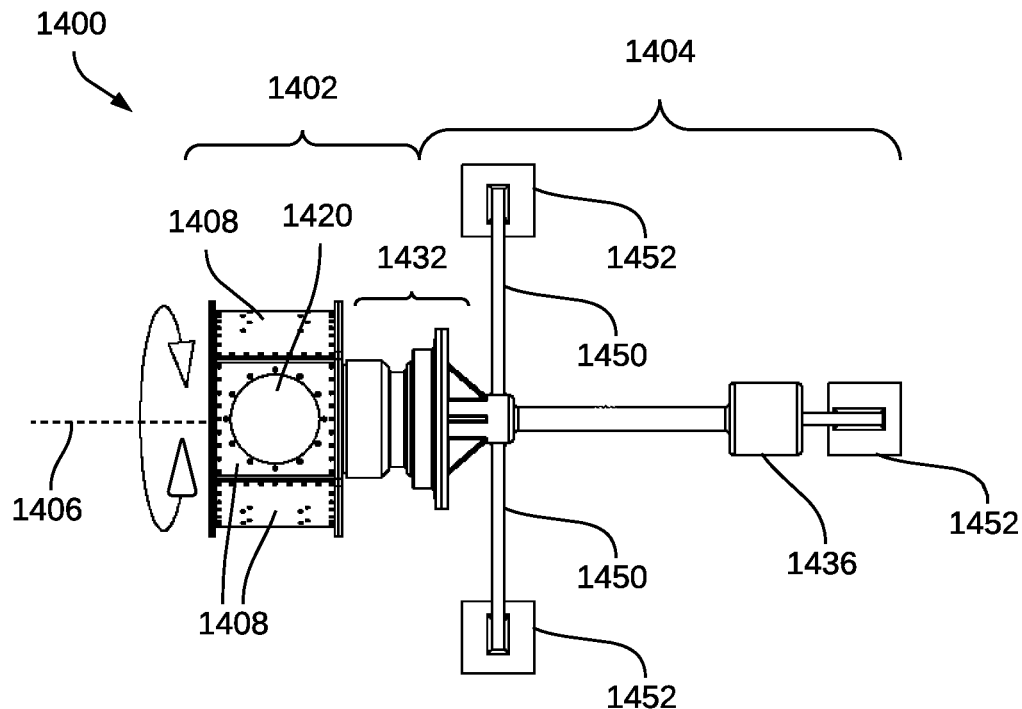
FIG. 14 illustrates a top view of a system for remote sensing, according to an embodiment.

Turning now to FIG. 14, another exemplary system for remote sensing is illustrated, in accordance with an embodiment. FIG. 14 shows a top view of a system 1400, which includes a mobile body portion 1402 and a fixed body portion 1404. Mobile body portion 1402 is rotatable about a rotation axis 1406, and also includes a plurality of faces 1408. One or more of the plurality of faces 1408 includes a radiometer 1420 integrated therein. Faces 1408 can include additional radiometers, wherein the additional radiometers are identical to radiometer 1420 or have different characteristics, such as to be sensitive to different electromagnetic radiation bands from radiometer 1420.

Fixed body portion 1404 of system 1400 includes a coupler arrangement 1432 configured for rotatably coupling mobile body portion 1402 thereto. Coupler arrangement 1432 includes, for instance, a motor mechanism for providing power to rotate mobile body portion 1402. Fixed body portion 1404 further may include a counter weight 1436 for providing counterbalance and system stability to the weight of mobile body portion 1402 when attached to fixed body portion 1404. Fixed body portion 1404 further includes several legs 1450 and feet 1452 for attaching system 1400 to a surface. In addition, an azimuthal motion (not shown) can be included to enable scanning the whole hemisphere above and below radiometer.

Figure 15:
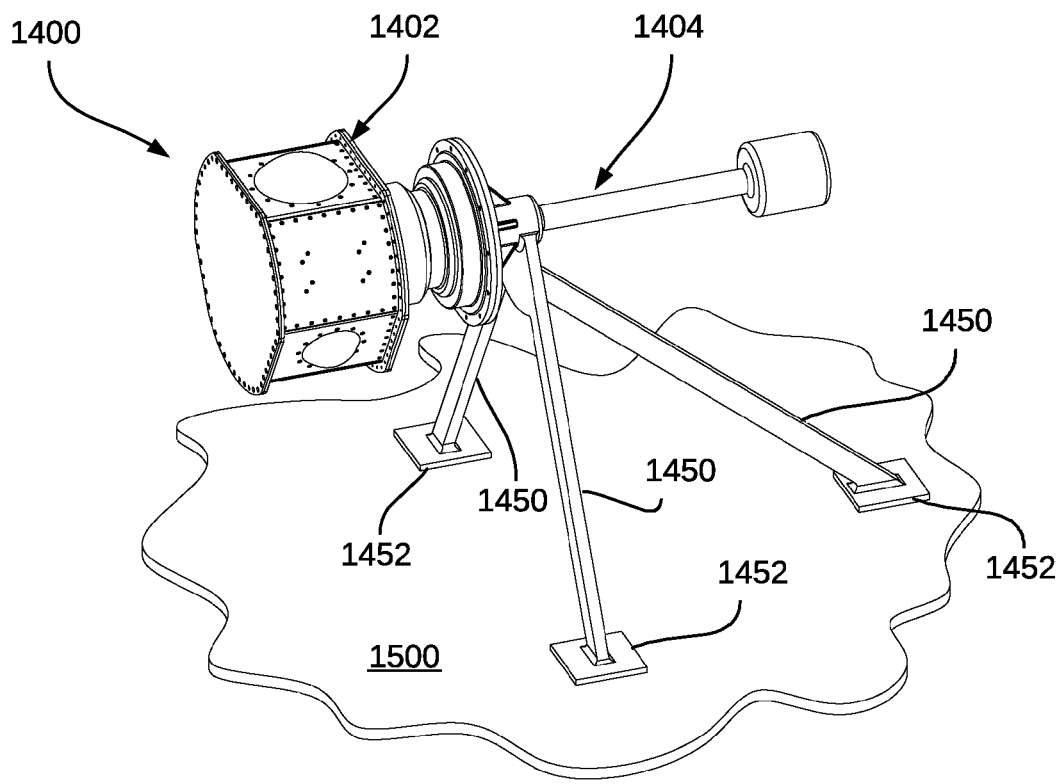
FIG. 15 illustrates a perspective view of the system of FIG. 14.

FIG. 15 illustrates a perspective view of system 1400 of FIG. 14, shown here to illustrate how feet 1452 can be attached to a surface 1500. Surface 1500 may be, for instance, an outer shell of a watercraft, a motor vehicle, a building, or a lawn, a concrete surface, or another object. Optionally, legs 1450 and feet 1452 can be configured for attachment to a specific surface as needed.

Figure 16:
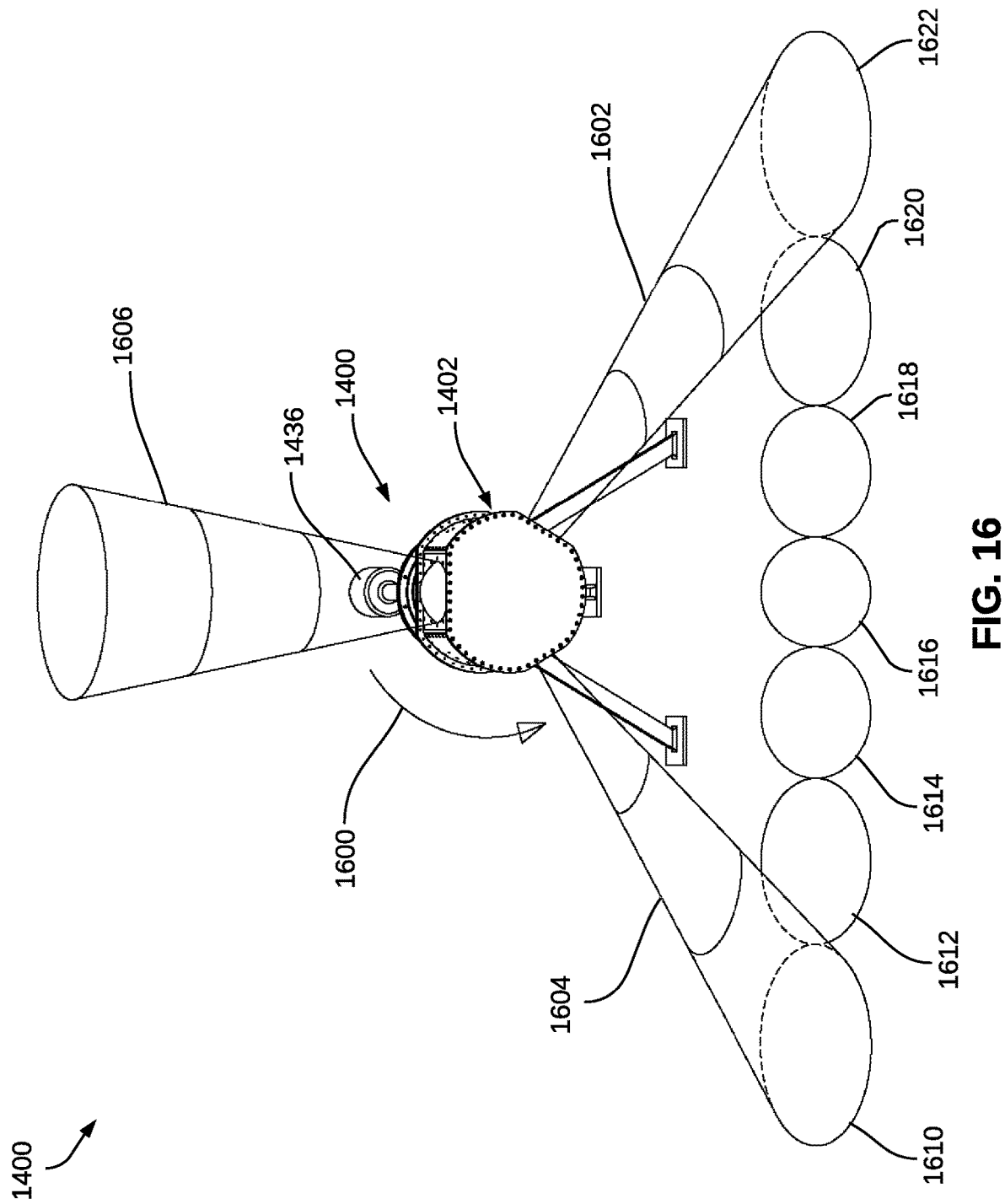
FIG. 16 illustrates the system of FIG. 14 observing an environment in an elevation mode by receiving electromagnetic radiation from multiple radiometer antenna beams of the system while a mobile body portion of the system is rotating about an axis of rotation of the mobile body portion.

FIG. 16 illustrates the system of FIG. 14 observing an environment in an elevation mode by receiving electromagnetic radiation from multiple radiometer antenna beams of the system while a mobile body portion of the system is rotating about an axis of rotation of the mobile body portion. As shown in FIG. 16, as mobile body portion 1402 of system 1400 is rotated in a direction indicated by an arrow 1600, antenna beams 1602, 1604, and 1606, corresponding to different radiometers mounted within mobile body portion 1402, perform observations over adjacent footprints 1610, 1612, 1614, 1616, 1618, 1620, and 1622. Thus, antenna beams 1602, 1604, and 1606 can observe at various frequency bands over the same areas. For any state of the atmosphere, the polarization signal should be substantially the same for horizontal and vertical polarizations at zenith. Thus, if one of the radiometers installed within mobile body portion 1402 may be malfunctioning (e.g., as confirmed by a dual polarization zenith-looking process performed by a dual polarization radiometer), the mis match of the horizontal and vertical polarization signals can indicate the malfunction (e.g., calibration or other drift) of a radiometer. Also, since antenna beams 1602, 1604, and 1606 point in different directions, multiple areas can be simultaneously observed. For example, if two radiometers are installed on faces separated by 120 degrees within mobile body portion 1402, and body portion 1402 is rotated at a rotational speed of two rotations per second, the two radiometers can sample the same footprint within approximately 167 milliseconds. Such rotational configurations may be useful for example, when the observed environment is an atmosphere and/or a surface since variations in the characteristics of the atmosphere and/or surface may be negligible over these periods of time. Alternatively, system 1400 may be designed such that the observational delay between various antennas footprints will be negligible, for example, by appropriately adjusting the scanning period, speed of rotation, antenna beamwidth (footprint), etc.

Figure 18:
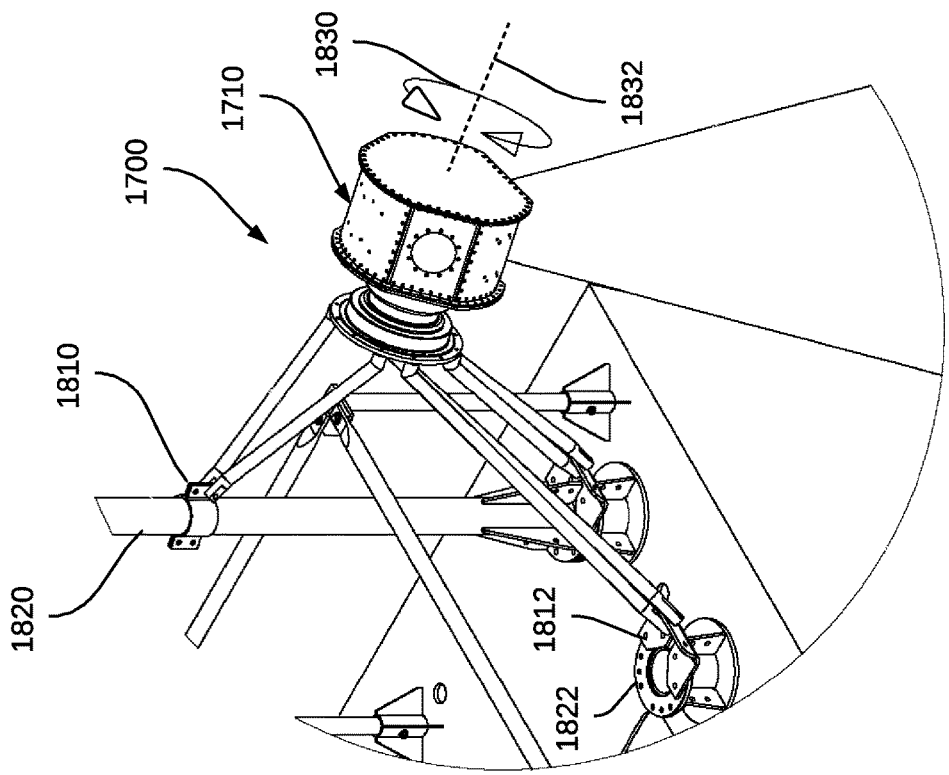
FIG. 18 illustrates an enlarged view of the system of FIG. 17.
Figure 17:
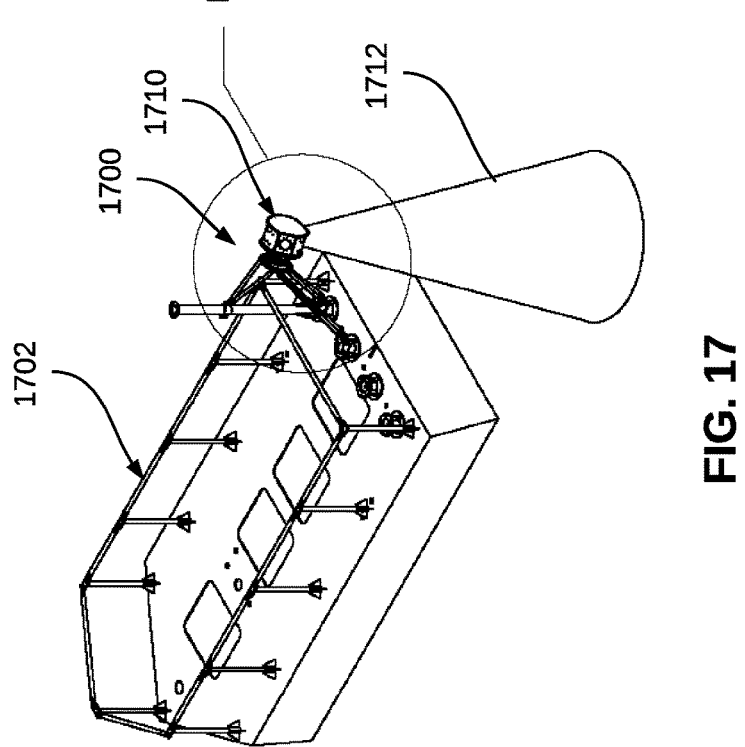
FIG. 17 illustrates a perspective view of the system of FIG. 14 installed on a nautical buoy.

FIG. 17 shows a perspective view of a modified environmental monitoring system of FIG. 14 as installed on a nautical buoy, and FIG. 18 illustrates an enlarged view of the system of FIG. 17. As shown in FIG. 17, a modified system 1700 is installed on a nautical buoy 1702. As visible in FIG. 18, feet 1810 and 1812 of system 1700 has been modified from the system illustrated in FIGS. 14-16 to facilitate attachment to a post 1820 and hardware 1822, respectively. System 1700 is installed on nautical buoy 1702 such that mobile body portion 1710 is rotatable (as indicated by a double-headed arrow 1830) along a rotation axis 1832 parallel to the surface of the body of water in which nautical buoy 1702 is deployed. At least one of the radiometers (not visible) installed within mobile body portion 1710 is configured for observing the environment in an antenna beam 1712. Additional radiometers installed within mobile body portion 1710 can be configured for observing the environment through additional antenna beams.

Notably, radiometers installed within mobile body portion 1710 are positioned with an unobstructed view of the ocean surface as well as the atmosphere. When mobile body portion 1710 is rotated at a sufficient rotational speed (e.g., 2 rotations per second), the observing radiometer can complete one scan of the water surface and the atmosphere quickly, for example in 0.5 second. During such a short duration of time, the motion of nautical buoy 1702, particularly its attitude changes, is considered negligible and no additional compensation for motion of the nautical buoy is required. Thus, system 1700 does not require complex and energy demanding motion compensation mechanisms required by other conventional remote sensing systems.

Particularly in installations of remote sensing systems in water environments, microwave bands of the electromagnetic spectrum are affected by the presence of water. Therefore, in addition to protecting the internal instrumentation (e.g., radiometer, motor, and other mechanisms) from the body of water, preventing condensation and other types of water collection on the external optical surfaces (for example, antenna lenses) of the instrumentation is an important aspect of deployment of the disclosed remote sensing systems in water-rich environments. Advantageously, aerodynamic forces and centripetal forces acting on radiometers and instrumentation installed within mobile body portion 1710 also serve to prevent water from remaining on the surface of any lenses/covers, thus enabling long term (i.e., months or years) use of the remote sensing system of the present disclosure even in ocean environments. Moreover, the aerodynamic and centrifugal forces serve to remove dirt, salt, and other obstructions from the viewing windows of the radiometers. Thus, the radiometers installed in mobile body portion 1710 can be protected from condensation and other undesirable sources of water contamination, and system 1700 is operable even in water-rich environments. Further cost savings can be attained by eliminating the need for expensive hydrophobic coatings and/or air blowers and other condensation management mechanisms.

An additional advantage of the embodiments illustrated above is that they allow improved calibration and maintenance protocols over conventional remote sensing systems. Currently available remote sensing systems require two or more calibration targets (manmade, artificial target) at different temperatures to calibrate and subsequently maintain measurement accuracy of the remote sensing instruments, such as radiometers. For example, for a given environment to be observed with a given expected temperature range, a first calibration target at a lower end of the expected temperature range (i.e., a cold target, cooled by boiling liquid nitrogen) and a second calibration target at a higher end of the expected temperature range (i.e., a hot target) are required to serve as reference targets for monitoring any gain and offset fluctuations of the radiometers. The first and second calibration targets can be located internally within or external to the remote sensing system. Internal calibration targets can include reference loads and/or electrical noise sources configured for monitoring the gain and offset fluctuations of the remote sensing instruments, such as an attenuator at ambient temperature as the cold target and a noise source as the hot target. An external calibration target can include a target located within the environment being observed with known temperature and emission characteristics and is sometimes referred to as a vicarious or ambient calibration target. Alternatively, external calibration targets can include artificial, manmade calibration targets. It is noted that, in some instances, reliance on such artificial targets can be problematic due to the difficulty of maintaining thermal stability and surface emission (e.g., due to various dirt accumulation on optical surfaces), of such artificial targets, or availability of cryogenic gases such as liquid nitrogen.

Several external (i.e., vicarious) calibration techniques are frequently used by persons skilled in the art of remote sensing. For example, a tipping calibration (as described, for example, in Han, Y., & Westwater, E. R. (2000, May), "Analysis and improvement of tipping calibration for ground-based microwave radiometers," *IEEE Transaction on Geoscience and Remote sensing*, 38(3), 1260-1277, and Liljegren, J. C. (1999), "Automatic Self-Calibration of ARM Microwave Radiometers," *Ninth ARM Science Team Meeting Proceedings*. San Antonio, Texas: DOE ARM.) can be performed by observing an environment in an elevation mode beginning at zenith (i.e., approximately normal to and facing away from the earth's surface) and scanning away from the zenith. Tipping calibrations can provide particularly accurate calibration at low optical depths (i.e., for optically transparent channels), and work well for transparent microwave channels, such as channels below 18 GHz, and a 22 GHz, 30 GHz, 50 GHz, or 89 GHz channel, under clear sky conditions. In tipping calibration, a brightness temperature of an environment in a transparent microwave channel is known to depend on the angle of observation, such that the brightness temperature is expected to be the lowest at zenith, then increase as the observation angle deviates from zenith, thus allowing the observed brightness temperature variation as the basis of calibration. Other external calibration techniques, such as horizontal-look calibration, surface calibration using a well-known surface (e.g., with known emission coefficient and temperature), dual polarization calibration, sky-look calibration (on aircraft, almost above the atmosphere zenith look), spiral ascent and descent calibration (when airborne), can also be used. Additional vicarious calibration opportunities include sun or lunar look (sun or moon transition through an antenna beam) and a retrieval of integrated water vapor by a co-located GPS receiver. These vicarious calibrations replace man-made external targets and can be used in the aforedescribed systems, such as 100, 700, 1400 and similar, for maintaining the accuracy of internal calibration references for each radiometer.

Advantageously, the remote sensing systems disclosed herein can be calibrated using one or more modes of external and/or internal calibration methods. Particularly, the rotatability of the remote sensing systems disclosed herein make the embodiments described herein uniquely well suited for performing one or more of the known external calibration techniques. Such calibration protocols can be performed autonomously, without intervention by an operator, such that the embodiments of remote sensing systems described herein can be deployed for an extended period of time (e.g., multiple months) at remote locations (e.g., on a buoy) without requiring manual calibration with an artificial external target.

In many embodiments, the remote sensing systems disclosed herein can rely on internal reference targets for regularly scheduled calibrations (e.g., performed at scheduled intervals, such as hundreds or thousands of times per second, once every hour, every few hours, etc.), and also use external (i.e., vicarious) calibration targets at predetermined or opportunistic intervals to maintain accuracy of the internal reference targets. For example, the early morning hours before sunrise can be an opportune time to calibrate the internal reference targets using external calibration, by a tipping calibration. By using a combination of frequent calibration with internal reference targets and opportunistic calibration using external reference targets, the radiometer calibration is maintained over varying operating temperature range and the requirements for thermal stabilization of the internal reference targets and/or the radiometer can be relaxed. Accordingly, the manufacturing costs, design complexity, and energy consumption of the embodiments of the remote sensing system described herein can be reduced with respect to currently available, conventional remote sensing systems. In addition, maintenance and ownership cost of such remote sensing system is significantly lowered, since no user intervention is needed for keeping the radiometer calibrated.

For instance, when the embodiments of the remote sensing systems described herein are operating in an elevation mode such that the mobile body portion is rotated about a rotation axis parallel to the surface of the earth (e.g., as shown in FIGS. 6, 13, 16, 17, and 18), the remote sensing instruments contained within the mobile body portion can observe the complete sky from horizon to horizon. As a result, clear sky conditions can be identified by the symmetry of observations with respect to the zenith position. The embodiments of each radiometer described herein can also be built, for example, in a way that they contain at least one transparent channel for facilitating the performance of tipping calibration.

When the embodiments of the remote sensing systems described herein are operable in multiple frequency channels, a combination of different external calibration techniques can be used to improve the remote sensing instrument calibration. For example, a channel at or below approximately 50 GHz would serve as a transparent channel suitable for calibration by tipping calibration techniques. For channels at or around 60 GHz, opaque channels, a horizontal-look calibration technique can be used (i.e., the ambient temperature of the atmosphere is assumed to be equal to radiated temperature). A surface calibration technique can also be performed (assuming known temperature and emission coefficient of the surface under the system) for one or both of the above channels as well. Optionally, one or more of the remote sensing instruments in the embodiments of the remote sensing systems described herein can be configured such that all of the receiver parts corresponding to the various frequency channels share the same active components and are approximately simultaneously sampled, such that the offset and gain over all of the channels are correlated. Assuming any variation of the lenses and protective covers over the remote sensing instruments are also correlated, a predetermined correlation function can be developed such that a calibration of one radiometer channel can be transferred to the calibration of every other channel.

Figure 19:
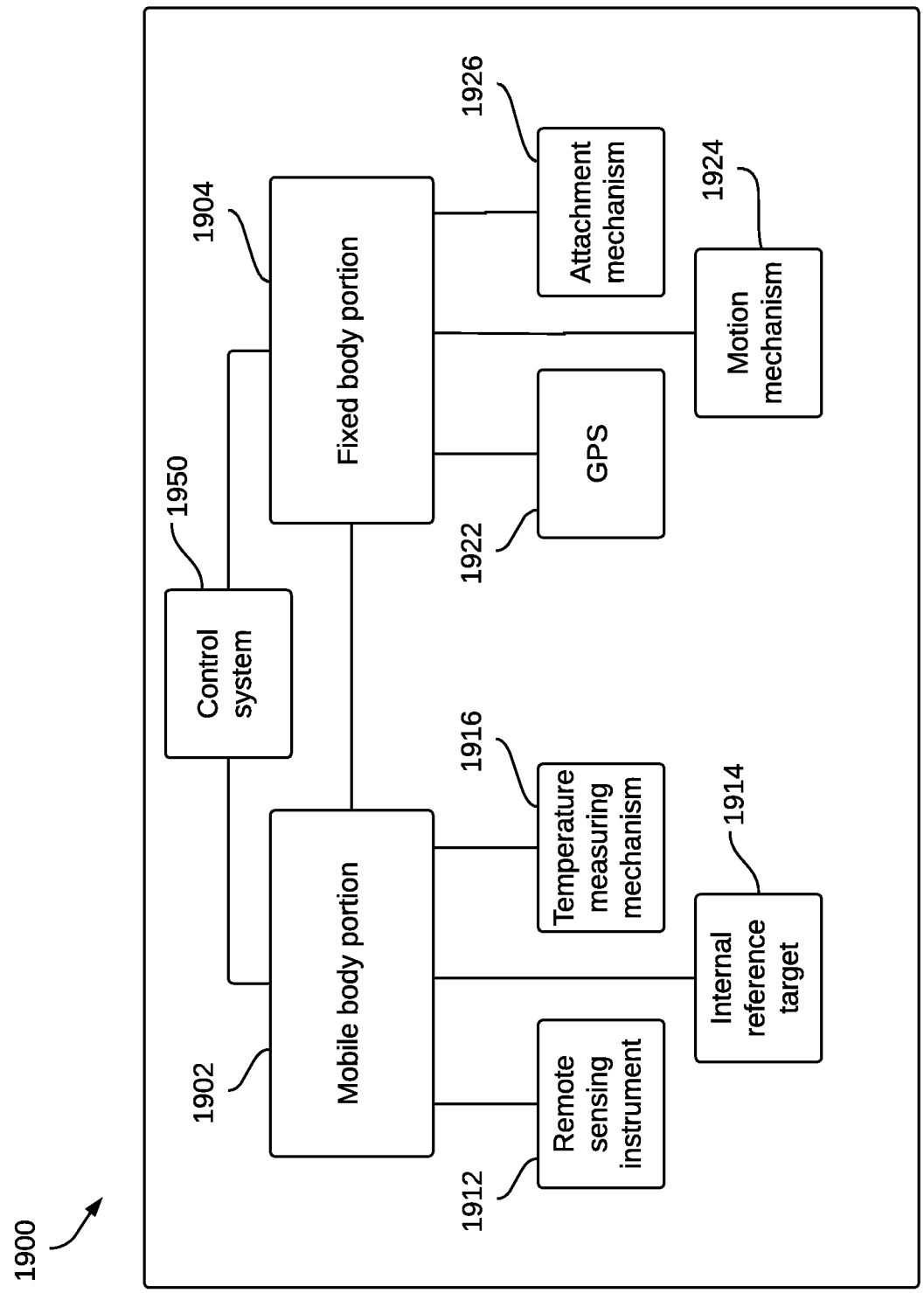
FIG. 19 illustrates an exemplary remote sensing system, in accordance with an embodiment.

FIG. 19 shows the components of an exemplary environmental sensing system, in accordance with an embodiment. Like the various embodiments of the environmental sensing systems described above, an environmental sensing system 1900 includes a mobile body portion 1902, which is rotatably attached to a fixed body portion 1904. Mobile body portion 1902 includes one or more remote sensing instrument 1912. While only one block 1912 is shown in FIG. 19, it is to be understood that additional remote sensing instruments, such as radiometers, can be integrated with mobile body portion 1902. Mobile body portion 1902 optionally includes one or more internal reference target 1914. Again, more than one internal reference targets can be integrated with mobile body portion 1902, for example for different wavelength/frequency bands. Mobile body portion further optionally includes one or more temperature measuring mechanism 1916. Temperature measuring mechanism 1916 can be used, for example, for measuring a temperature of internal reference target 1914 as part of a calibration process, as described below.

Fixed body portion 1904 may include a GPS system 1922 (e.g., providing positioning, navigation, and timing information), a motion mechanism 1924, and an attachment mechanism 1926. Motion mechanism 1924 includes, for instance, a motor for effecting motion of mobile body portion 1902, and associated gears, sprockets, or other components related to motion of mobile body portion 1902. Attachment mechanism 1926 can include, for example, a receiving element (e.g., FIGS. 1, 4, and 9) or one or more feet (e.g., FIGS. 14-16, 18). Other attachment mechanisms, such as clips and fixtures, are also possible depending on the use scenario. Fixed body portion 1904 is configured to rotatably couple to mobile body portion 1902 such that mobile body portion 1902 is freely rotatable with respect to fixed body portion 1904. In this way, system 1900 is able to provide a full 360-degrees vertical scan, thus enabling continuous vertical (or azimuthal) scanning over a much larger observational area than currently possible with conventional sensing devices. The rotatability of mobile body portion 1902 enables a variety of environmental sensing applications as well as the implementation of advantageous calibration methods, as described below. Finally, a control system 1950 controls the operation of mobile body portion 1902 and fixed body portion 1904 including, but not limited to, handling of measured signals obtained from remote sensing instrument 1912, monitoring and calibration of internal reference targets 1914, calibration of remote sensing instrument 1912, operating temperature measuring mechanism 1916, monitoring the readings obtained at GPS 1922, controlling the motion of mobile body portion 1902 via motion mechanism 1924, monitoring the status of attachment mechanism 1926, and monitoring the status of various components of environmental sensing system 1900. While control system 1950 is shown as separate from mobile body portion 1902 and fixed body portion 1904 in FIG. 19, it is understood that control system 1950 can be integrated into, for example, mobile body portion 1902 and/or fixed body portion 1904.

Figure 20:
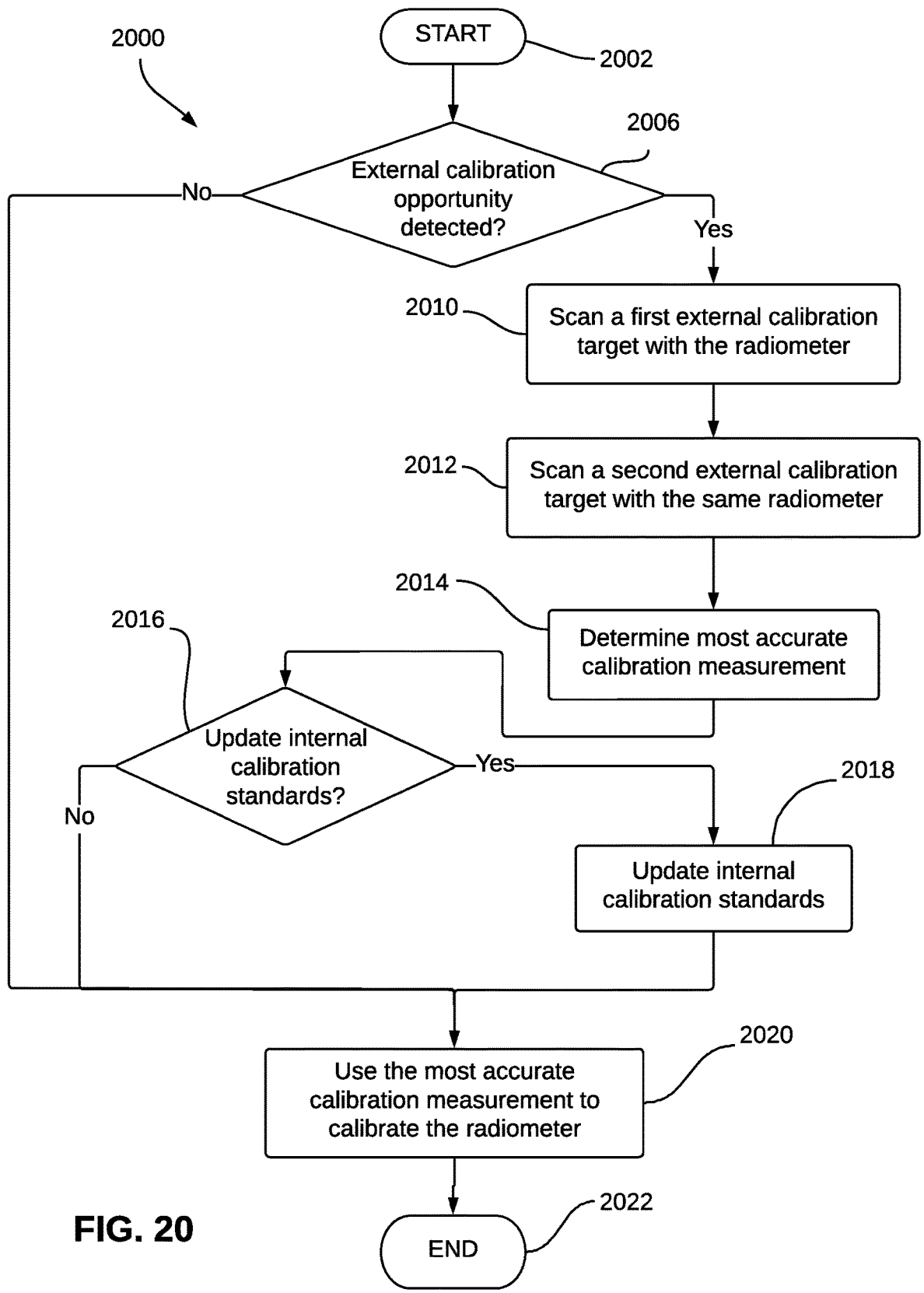
FIG. 20 illustrates a flow chart for an embodiment of a method of calibrating a system for remote sensing.

FIG. 20 is a flow chart illustrating a method for calibrating a remote sensing system, such as those illustrated herein, in accordance with an embodiment. As shown in FIG. 20, a calibration process 2000 is initiated in a start step 2002. A decision 2006 is then made whether an external or vicarious calibration opportunity has been detected. If the answer to decision 2006 is "Yes," an external or vicarious calibration opportunity (such as tipping calibration, sun transition, or other) has been detected, then scanning of a first external calibration target with radiometers (to be calibrated) of the remote sensing system is performed, step 2010. The temperature of a second external calibration target is determined by scanning the second external calibration target with the radiometer in a step 2012. Then the most accurate calibration measurement is used in a step 2014 to compare the existing internal calibration standard with the updated one, based on the new calibration measurements. A decision 2016 is made on whether or not to adjust internal calibration standards and use the newly obtained values. The most accurate calibration measurement, based on the scans of the first and second external calibration targets as well as on the existing internal calibration standard, is determined in a step 2016. If the newly obtained calibration is accepted as the most accurate calibration measurement, then the internal calibration standards are updated in a step 2018. The radiometer is then calibrated, based on the most accurate calibration measurement in a step 2020. This process may be executed in parallel or in series for every radiometer in the remote sensing system, or only for a subset of the radiometers within the system. The updated internal calibration standards based on the current most accurate calibration measurement is used until the next calibration opportunity is detected.

Thus, as illustrated in FIG. 20, the most recent external calibration provides an update (i.e., check) on the internal calibration standards of each radiometer as often as practical or desired. As an example, an algorithm for tracking these calibration accuracies may be used to monitor the calibration status of the remote sensing system. For instance, such an algorithm may store a list of previous calibration values and prevent a wrong value from step 2016 from being used in the calibration process. Artificial intelligence algorithm may also be used to implement or enhance process 2000. It is noted that scanning of the internal calibration target may occur outside of the illustrated process 2000, for example, on a periodical schedule or ad hoc.

The calibration processes described in FIG. 20 can be implemented, for example, by controller 1950 described in relation to FIG. 19.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, an environmental sensing system as described above can be configured to observe with its axes aligned with the Earth axis and thus provide retrievals of the radiant flux of electromagnetic radiation in multiple polarization from multiple angles without disturbance of the naturally occurring polarization signal in the observed environment. An environmental sensing system as described above may be configured to provide protection of a radiometer optical surfaces (e.g., antenna lens) from water and hydrometeors during operation. An environmental sensing system as describe above may be configured to include any number of radiometers in one instrument with co-located beams that can observe a scene (i.e., environment) at the same time, or practically the same time, with the same polarizations. Similarly, in an embodiment, an environmental sensing system as described above can be calibrated without applications (or use) of man-made (artificial) targets (although a use of some man-made target is not excluded). Further, an environmental sensing system as described above may implement any other microwave radiometer calibration method that is autonomous and does not require user intervention, participation, interaction, or application of special targets, such as cryogenically cooled targets. An environmental sensing system as described above may be capable of detecting a malfunction of its sensor by using a dual polarization zenith looking process, where the observed signal has to be the same under all conditions such that any difference in the observed signals may be indicative of either a faulty calibration or other sensor (i.e., radiometer) problems. Moreover, an environmental sensing system as described above may provide an imaging and sounding observations from the same platform, using the same instrument, such as discussed in relation to system 700. An environmental sensing system as described above may reliably operate in challenging conditions, such as near an ocean surface and under precipitation.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

What is claimed is:

1. A system for passive microwave remote sensing using at least one microwave radiometer, the system comprising:
a fixed body portion, the fixed body portion being configured to attach to a mobile platform; and
a mobile body portion, the mobile body portion being configured for rotatably coupling with the fixed body portion for rotation about a rotation axis, wherein the mobile body portion is configured for supporting the at least one microwave radiometer therein such that the at least one microwave radiometer rotates about the rotation axis when the mobile body portion is rotated about the rotation axis such that a polarization axis of the at least one radiometer is aligned with an earth axis, and wherein the fixed body portion includes a motor mechanism for effecting rotation of the mobile body portion such that the at least one microwave radiometer provides a vertical scanning below and above the mobile platform.

2. The system of claim 1, wherein the at least one microwave radiometer is configured for providing at least a 180-degrees continuous vertical scan.

3. The system of claim 2, wherein the at least one microwave radiometer is configured for providing a full 360-degrees continuous vertical scan.

4. The system of claim 1, wherein the mobile body portion comprises a first body section supporting a first microwave radiometer configured to operate at a first band of electromagnetic spectrum, wherein the mobile body portion comprises a second body section supporting a second microwave radiometer configured to operate at a second band of electromagnetic spectrum, different from the first band, and wherein the first body section is configured to be independently rotatable with respect the second body section.

5. The system of claim 4, wherein the first microwave radiometer is a dual polarization radiometer configured for obtaining and comparing a horizontal polarization signal and a vertical polarization signal obtained at zenith, and wherein a comparison of the horizontal polarization signal and the vertical polarization signal obtained by the first microwave radiometer provides an indication of a malfunction of the second microwave radiometer.

6. The system of claim 5, wherein the indication of the malfunction of the second microwave radiometer is provided without performing a calibration of the first and second microwave radiometers.

7. The system of claim 4, wherein at least one of a scanning period, a speed of rotation, and an antenna beamwidth of the first body section is independently adjustable with respect to the second body section.

8. The system of claim 1, wherein the mobile body portion comprises a first body section supporting a first microwave radiometer configured to operate at a first band of electromagnetic spectrum, wherein a second microwave radiometer is also configured to operate at the first band of electromagnetic spectrum to provide at least one of higher spatial resolution and improved sampling performance as compared to another system without the second microwave radiometer.

9. The system of claim 1, further comprising an internal reference target, and a temperature measuring mechanism, wherein the at least one microwave radiometer is configured for observing an external calibration target and obtaining an external calibration measurement, and wherein the temperature measuring mechanism is configured for observing the internal reference target and obtaining an internal calibration measurement.

10. The system of claim 1, wherein the at least one microwave radiometer is configured for observing a first external calibration target and obtaining a first external calibration measurement, wherein the at least one microwave radiometer is configured for observing a second external calibration target and obtaining a second external calibration measurement.

11. The system of claim 1, wherein the fixed body portion includes a coupler arrangement configured for rotatably coupling the mobile body portion thereto.

12. The system of claim 11, wherein the fixed body portion further includes a counter weight for providing counterbalance and system stability to a weight of the mobile body portion when rotatably coupled with the fixed body portion.

13. The system of claim 1, wherein the mobile body portion is rotated at a rotational speed of at least two rotations per second.

14. The system of claim 1, wherein the system is installed in a water environment, and wherein the mobile body portion is rotated at a sufficient rotational speed to provide aerodynamic and centrifugal forces to remove obstructions from a viewing window of the at least one microwave radiometer.

15. A method for calibrating a passive microwave remote sensing system, the method comprising:

providing a fixed body portion and a mobile body portion as part of the passive microwave remote sensing system, wherein the fixed body portion is configured to attach to a mobile platform, and wherein the mobile body portion is configured for supporting at least one microwave radiometer therein and is rotatably coupled with the fixed body portion for rotation about a mobile body axis over a range of rotation angles;

rotating the at least one radiometer about the mobile body axis while sensing incoming radiant flux of electromagnetic radiation incident thereon over the range of rotation angles; and using the incoming radiant flux so sensed to calibrate the passive microwave remote sensing system by at least one of tipping calibration, horizontal-look calibration, surface calibration, dual polarization calibration, sky-look calibration, spiral ascent and descent calibration, sun look calibration, lunar look calibration, and integrated water vapor retrieval calibration.

16. The method of claim 15, wherein using the incoming radiant flux to calibrate the passive microwave remote sensing system is performed autonomously, without intervention by an operator.

17. The method of claim 15, wherein the passive microwave remote sensing system includes an internal reference target, and the method further comprising using the incoming radiant flux so sensed to correlate with the internal reference target.

18. The method of claim 15, wherein providing the fixed body portion and the mobile body portion further comprises configuring the mobile body portion to include a first body section supporting a first microwave radiometer and a second body section supporting a second microwave radiometer, the method further comprising:

collecting at the first microwave radiometer the incoming radiant flux of electromagnetic radiation incident thereon; and using the incoming radiant flux of electromagnetic radiation so collected at the first microwave radiometer to perform a calibration of the second microwave radiometer.

* * * * *